US008269062B2

(12) United States Patent
Katavic et al.

(10) Patent No.: US 8,269,062 B2
(45) Date of Patent: Sep. 18, 2012

(54) LUNARIA ANNUA, CARDAMINE GRAECA AND TEESDALIA NUDICAULIS FAE GENES AND THEIR USE IN PRODUCING NERVONIC AND EICOSENOIC ACIDS IN SEED OILS

(75) Inventors: Vesna Katavic, Vancouver (CA); Elzbieta Mietkiewska, Edmonton (CA); David C. Taylor, Saskatoon (CA); Yiming Guo, Saskatoon (CA); Jennifer M. Brost, Saskatoon (CA)

(73) Assignee: National Research Council of Canada, Ottawa, ON ( * ) Notice: Subject to any disclaimer, the term of this patent is extended or adjusted under 35 U.S.C. 154(b) by 448 days.

(21) Appl. No.: 12/312,650

(22) PCT Filed: Nov. 21, 2006

(86) PCT No.: PCT/CA2006/001911
§ 371 (c)(1),
(2), (4) Date: Dec. 17, 2009

(87) PCT Pub. No.: WO2008/061334
PCT Pub. Date: May 29, 2008

(65) Prior Publication Data
US 2010/0122377 A1    May 13, 2010

(51) Int. Cl.
*A01H 1/00* (2006.01)
*A01H 5/00* (2006.01)
*A01H 5/10* (2006.01)
*C12N 5/14* (2006.01)
*C07H 21/04* (2006.01)

(52) U.S. Cl. ........ 800/278; 800/281; 800/298; 800/306; 800/312; 800/317.3; 800/320; 800/320.1; 800/320.2; 800/320.3; 800/322; 435/419; 536/23.6

(58) Field of Classification Search ........................ None
See application file for complete search history.

(56) References Cited

U.S. PATENT DOCUMENTS 6,124,524 A     9/2000  James, Jr. et al.
6,828,475 B1 * 12/2004  Metz et al. .................... 800/281

FOREIGN PATENT DOCUMENTS

| CA | 2391953  | 5/2001 |
| CA | 2547320  | 6/2005 |
| WO | 91/07955 | 6/1991 |
| WO | 96/05740 | 2/1996 |

OTHER PUBLICATIONS

Altschul S. F., Gish W., Miller W., Myers E.W. And Lipman D.J. (1990) Basic local alignment search tool. J Mol Biol 237: 182-192.
Appelqvist L.A. (1976) Lipids in Cruciferae. The Biology and the Chemistry of the CRUCIFERAE, Vaughan, J.G. and Macleod, A.J. (Eds.), Academic Press, London, UK, pp. 221-277.
Babic V., Datla R.S., Scoles G.J. and Keller W.A (1998) Development of an efficient Agrobacterium-mediated transformation system . . . Plant Cell Reports 17: 183-188.
Bradford M. M. (1976) A rapid and sensitive method for the quantitation of microgram quantities of protein utilizing . . . Anal. Biochem. 72, 248-254.
Chen J., Greenblatt I. M. and Dellaporta S. L. (1992) Molecular analysis of Ac transposition and DNA replication. Genetics 130: 665-676.
Clough SJ. and Bent A.F. (1998) Floral dip: a simplified method for Agrobacterium-mediated transformation of Arabidopsis thaliana. Plant J 16: 735-743.
Ghanevati M. and Jaworski J. G. (2001) Active-site residues of a plant membrane-bound fatty acid elongase β-ketoacyl-CoA synthase, FAE1 KCS. Bioch. et Bioph. Acta 1530, 77-85.
Jako C, Kumar A., Wei Y., Zou J-T.,Barton D.L.,Giblin E. M., Covello P. S. and Taylor D. C.(2001) Seed-specific over-expression of an Arabidopsis . . . Plant Physiol 126: 861-874.
Jart A. (1978) The fatty Acid Composition of various Cruciferous Seeds. J. Amer. Oil. Chem. Soc. 55: 873-875.
Katavic V., et al.(1995) Alteration of seed fatty acid composition by an ethyl methanesulfonate-induced mutation in Arabidopsis thaliana . . . Plant Physiol. 108, 399-409.
Katavic V. et al. (2001 ) Improving erucic acid content in rapeseed through biotechnology: what can the Arabidopsis FAE1 and the yeast SLC1-1 genes . . . Crop Science 41 , 739-747.
Katavic V., Barton D. L., Giblin, E. M, Reed D. W., Kumar A. and Taylor D.C. (2004) Gaining insight into the role of serine 282 in B. napus FAE1 . . . FEBS Letters 562: 118-124.
Koncz C. and Schell J. (1986) the promoter of TL-DNA gene 5 controls the tissue-specific expression of chimaeric genes by a novel type of Agrobacterium . . . Mol Gen Genet 204: 3.
Lassner M.V. (1997) Transgenic oilseed crops: a transition from basic research to product development. Lipid Technology, 9(1 ), 5-9.
Mastebroek H. D. and Marvin H.J. P. (2000) Breeding prospects of Lunaria annua L. Industrial Crops and Products 11 : 139-143.
Meier zu Beerentrup H. and Röbbelen G. (1987) Screening for European production of oilseeds with unusual fatty acids. Angew. Botanik 61 : 287-303. Meyer, A. et al. Novel fatty acid elongases and their use for the reconstitution of docosahexaenoic acid biosynthesis.J. Lipid Res.,2004.45:1899-1909.
Mietkiewska E., et al. (2004) Seed-specific heterologous expression of a nasturtium FAE gene in Arabidopsis results in a dramatic increase . . . Plant Physiol 136: 2665-2675.
Nicholls F. H. (1996) New crops in the UK: from concept to bottom line profits. In: Progress in New Crops, Janick, J. (Ed.), ASHS Press, Alexandria, VA.
Persson B. and Argos P. (1994) Prediction of transmembrane segments in proteins utilizing multiple sequence alignments. J Mol Biol 2Z7: 182-192.
Sargent J. R., Coupland K. and Wilson R. (1994) Nervonic Acid and Demyelinating Disease. Medical Hypotheses 42: 237-242.

*Primary Examiner* — Eileen B O Hara
(74) *Attorney, Agent, or Firm* — Hans Koenig

(57) ABSTRACT

This invention relates to nucleic acid sequences coding for a *Lunaria annua, Cardamine graeca* or *Teesdalia nudicaulis* fatty acid elongase, yeast cells expressing the genes/enzymes, plants themselves and cells of such plants and seeds which contain a heterologous gene coding for a *L. annua, C. graeca* or *T. nudicaulis* fatty acid elongase gene, the plant or seed being capable of producing increased proportion of a very long chain monounsaturated fatty acid, especially nervonic acid and eicosenoic acid, beyond that of a control plant or seed lacking the heterologous FAE gene or genes.

23 Claims, 10 Drawing Sheets

OTHER PUBLICATIONS

Taylor D. C, et al. (2001) Field-testing of transgenic rapeseed cv. Hero transformed with a yeast sn-2 acyltransferase results in increased oil . . . Mol Breeding 8: 317-322.

Whitfield, H. V. et al. (1993) Sub-Cellular Localization of Fatty Acid Elongase in Developing Seeds of the Lunaria Annua . . . Phytochemistry, vol. 32, No. 2, pp. 255-258.

Van Soest L.J.M. (1994) Alternative crop developments in the Netherlands. Alternative Oilseed and Fibre . . . Proceedings of a Workshop, Apr. 7-8, 1994 at Wageningen . . . pp. 14-20.

Cases et al. (1998) Identification of a gene encoding an acyl CoA:diacylglycerol acyltransferase, a key enzyme . . . Proc. Natl. Acad. Sci. USA vol. 95, pp. 13018-13023.

IPRP and WO on PCT-CA2006-001911, WO/2008/061334, May 13, 2010.

ISR on PCT-CA2006-001911, WO/2008/061334, May 29, 2008.

\* cited by examiner

LUNARIA ANNUA, CARDAMINE GRAECA AND TEESDALIA NUDICAULIS FAE GENES AND THEIR USE IN PRODUCING NERVONIC AND EICOSENOIC ACIDS IN SEED OILS

CROSS-REFERENCE TO RELATED APPLICATIONS

This application is a national entry of International Patent Application PCT/CA2006/001911 filed Nov. 21, 2006.

FIELD OF THE INVENTION

This invention is related to fatty acid elongase (FAE) genes, fatty acid elongases encoded by such genes, expression systems having such genes and uses of such genes for producing transgenic cells, seeds and plants having increased levels of very long chain monounsaturated fatty acids.

BACKGROUND OF THE INVENTION

Nervonic acid (cis-tetracos-15-enoic acid; 24:1) is a very long chain fatty acid (VLCFA). There is an increasing interest in production of nervonic acid (24:1 Δ15) for pharmaceutical and industrial applications (1, 2, 3). Nervonate plays a part in the biosynthesis of nerve cell myelin and it is found in sphingolipids of white matter in the human brain (and that of mammals). In diseases involving demyelination such as adrenoleucodistrophy (ALD) and multiple sclerosis (MS), there is a marked reduction of nervonic acid levels in sphingolipids. The administration of nervonic acid to sufferers of these diseases to alleviate the symptoms has been described (4). Nervonic acid has been investigated as a raw material in the pharmaceutical industry for production of medication used for symptomatic treatment of MS (5).

Despite the fundamental lack of understanding of the complexity and inter-relationships of many factors in human brain cells, there is an advantage in providing a supplement of nervonic acid in the diets of children. It is used in the food industry as a supplement to baby and infant formulas/food products (1). It seems to be beneficial to administer nervonic acid to adults whose nervonic acid levels are generally taken to be "normal", in particular women who intend to be pregnant, are pregnant or lactating (1).

Recently, there has been a strong interest from the University of Guelph and their associates in the Dairy Marketing Board and also at Martek, in high nervonate seed oils. More specifically, the University of Guelph has disclosed a use of nervonate-containing oil in cattle feed to improve the nutritional/health benefit qualities of expressed milk for human consumption (WO 2005036981, published Apr. 28, 2005). Again, the context is in enhanced neural development and as a prophylactic against neurodegenerative diseases. Clearly, an engineered seed oil high in nervonic acid could "spark" these lucrative spin-off utilities. Bioriginal Food and Science Corp. of Saskatoon has also expressed interest in high nervonate seed oil projects.

There are only a few species, most in the Brassicaceae, with high amounts of nervonic acid in their seed oil (6) but only *Lunaria annua* (syn. *Lunaria biennis* L; honesty or money plant) is grown as a niche crop. Honesty seed oil has 36-48% erucic but only 14 to 25% nervonic acid (5; our analyses). The oil itself without any chemical modification has been used on a small scale as an industrial lubricant (7, 8). However, this plant is a biennial. Seed yields between 1000 and 2000 kg/ha and an oil content of approximately 30% are low for a crop that needs a growing period of two years before harvest. Seed shattering is also a problem. Thus, it is uneconomical to grow *L. annua* as a major source of erucic acid or nervonic acid, even with set-aside payments (9). Breeding programs are ongoing in Europe financed by companies CPRO-DLO, VNK and CEBECO from the Netherlands, ADAS from UK, SIA from Spain and DKFZ from Germany to develop *L. annua* annual types. Although this research effort is progressing well, considerable effort will still be required to develop this crop for commercial use (10).

A *Brassica* species of special interest which we have identified for the first time to use for high nervonate technology is *Cardamine graeca* L or bittercress. *Cardamine* seed oil has from 9 to 10% erucic acid and from 43 to 54% nervonic acid (results from our analyses; 11). It is a small Mediterranean plant found growing on forest floors with red soil (terra rossa) in well sheltered areas. Because of the high level of nervonic acid in the seed oil, we have focused on this plant species and the seed-specific elongase gene FAE involved in biosynthesis of very long chain monounsaturated fatty acids (VLCMFAs). By expressing FAE in Brassicaceae we hope to develop edible oils enriched in nervonic acid which could be of interest to the food industry, for human consumption, or in the nutraceutical industry and as an additive in dairy-livestock feed to produce milk enriched in nervonic acid (12). Such oils should be high in nervonic acid but low (<10%) in erucic acid for acceptability in these markets.

VLCMFAs are synthesized outside the plastid by a membrane bound fatty acid elongation complex (elongase) using acyl-CoA substrates. The first reaction of elongation involves condensation of malonyl-CoA with a long chain substrate producing a 3-ketoacyl-CoA. Subsequent reactions are reduction to a 3-hydroxyacyl-CoA, dehydration to an enoyl-CoA, followed by a second reduction to form the elongated acyl-CoA. The 3-ketoacyl-CoA synthase (KCS) catalyzing the condensation reaction plays a key role in determining the chain length of fatty acid products found in seed oils and is the rate-limiting enzyme for seed VLCFMA production. The composition of the fatty acyl-CoA pool available for elongation and the presence and size of the neutral lipid sink are additional important factors influencing the types and levels of VLCFMAs made in particular cells.

Knowledge of the mechanism of elongation and properties of fatty acid elongase condensing enzymes is, in part, limited by their membrane-bound nature. As such they are more difficult to isolate and characterize than soluble condensing enzymes.

To date, increases in the content of some strategic fatty acids have been achieved by introduction of various fatty acid biosynthesis genes in oilseeds. Some examples include:
- expression of a medium chain fatty acid thioesterase from California Bay, in Brassicaceae to produce lauric acid (Calgene);
- expression of an anti-sense construct to the Δ9 desaturase in Brassicaceae to increase the stearic acid content (Calgene);
- use of co-suppression constructs encoding plant microsomal desaturases to increase proportions of oleic acid (DuPont/Cargill); and,
- expression of the *Arabidopsis* FAE1 gene in HEAR to increase the proportion of erucic acid by 10% or more (14).

There is some information on the FAE gene from *L. annua* (money plant). Lassner from Calgene stated that the heterologous expression of *L. annua* FAE in high erucic acid rapeseed (HEAR) apparently resulted in accumulation of approximately 20% nervonic acid in the seed oil (13). However, no data on *L. annua* FAE nucleotide and/or protein sequences were published and no data on *L. annua* FAE nucleotide and/or protein sequences were published and no data on experimental procedures were provided. Neither was there any accompanying report of the erucic acid content.

To date, no elongase genes have been isolated from *C. graeca* and characterized as encoding an elongase to produce nervonic acid. Similarly, not until the present invention has *Teesdalia nudicaulis* been identified as a source for a gene encoding an FAE for producing oils enriched in eicosenoic acid. To date, there is no published data, to our knowledge, on *T. nudicaulis* FAE sequence and its utilization.

Commonly owned PCT international patent application PCT/CA2004/002021 filed Nov. 24, 2004 discloses FAE genes cloned from nasturtium and *Crambe*. An elongase gene (FAE1) from *Arabidopsis* was cloned and published as James, D. W. Jr., Lim, E., Keller, J., Plooy, I., Ralston, E. and Dooner, H. K., "Directed tagging of the *Arabidopsis* FATTY ACID ELONGATION1 (FAE1) gene with the maize transposon activator". *The Plant Cell* 7: 309-319 (1995). Other related prior art includes: sequence ID NOs: 7, 9, 11, 13, 15, 17, 19, 21, 23, 25, 27, 29, 35, 37, 39, 41 from Jaworski, J. G. and Blacklock, B. J., world patent publication WO0194565 published Dec. 13, 2001; sequence ID NOs: 2, 4, 6, 12, 14, and sequences ID NO: 1, 3, 5, 7, 9, 11 and 13 from Jaworski et al., U.S. Pat. No. 6,307,128 issued Oct. 3, 2001; and, sequence ID NOs: 19, 20, 21, 22, 23 from Kunst and Clemens, world patent publication WO0111061 published Feb. 15, 2001.

SUMMARY OF THE INVENTION

In one aspect of the invention, there is provided an isolated nucleic acid sequence that encodes a polypeptide sequence that corresponds to a *Lunaria annua, Cardamine graeca* or *Teesdalia nudicaulis* fatty acid elongase (FAE) protein.

In another aspect of the invention, there is provided an expression system comprising a nucleic acid sequence coding for a *Lunaria annua, Cardamine graeca* or *Teesdalia nudicaulis* fatty acid elongase operably linked to a suitable promoter.

In another aspect of the invention, there is provided a cell comprising one or more heterologous nucleic acid sequences that encode a polypeptide corresponding to *Lunaria annua, Cardamine graeca* and/or *Teesdalia nudicaulis* fatty acid elongase.

In another aspect of the invention, there is provided a seed comprising one or more heterologous nucleic acid sequences that encode a polypeptide corresponding to *Lunaria annua, Cardamine graeca* and/or *Teesdalia nudicaulis* fatty acid elongase.

In another aspect of the invention, there is provided a plant comprising one or more heterologous nucleic acid sequences that encode a polypeptide corresponding to *Lunaria annua, Cardamine* graeca and/or *Teesdalia nudicaulis* fatty acid elongase.

In another aspect of the invention, there is provided a process for increasing level of very long chain monounsaturated fatty acids in a seed oil of a plant seed beyond that of a control seed, the process comprising transgenically expressing a polypeptide corresponding to *Lunaria annua, Cardamine graeca* and/or *Teesdalia nudicaulis* fatty acid elongase in a plant producing the seed, the control seed lacking expression of a polypeptide corresponding to *Lunaria annua, Cardamine graeca* and *Teesdalia nudicaulis* fatty acid elongase.

In another aspect of the invention, there is provided a process of obtaining seeds, the process comprising: a) transforming a plant cell with a recombinant nucleic acid construct comprising a nucleic acid sequence that encodes a polypeptide corresponding to *Lunaria annua, Cardamine graeca* or *Teesdalia nudicaulis* fatty acid elongase and a promoter for driving expression of the nucleic acid sequence in the plant cell to form a transformed plant; b) regenerating the transformed plant for one or more generations; and, c) harvesting seeds from cultivated plants produced in part b).

In another aspect of the invention, there is provided a seed having elevated levels of very long chain monounsaturated fatty acids and produced by a plant having one or more heterologous nucleic acid sequences that encode a polypeptide corresponding to *Lunaria annua, Cardamine graeca* and/or *Teesdalia nudicaulis* fatty acid elongase.

FAE genes from *Lunaria annua* (money plant), *Cardamine graeca* (bittercress) and *Teesdalia nudicaulis* encode FAE proteins (enzymes) that are involved in the elongation of fatty acids to produce very long chain monounsaturated fatty acids (VLCMFA), particularly nervonic acid (24:1 Δ15) and eicosenoic acid (20:1 Δ11). Cells, seeds and plants transformed with a heterologous FAE gene from *L. annua, C. graeca* or *T. nudicaulis* produce elevated levels of VLCMFA, especially nervonic and eicosenoic acids. Seed oils extracted from transformed seeds are highly enriched in such VLCMFAs. *L. annua* and *C. graeca* FAE are particularly effective at increasing levels of nervonic acid. *T. nudicaulis* FAE is particularly effective at increasing levels of eicosenoic acid.

Heterologous expression of one or more of the FAE nucleic acid sequences of the present invention in a cell, seed or plant increase levels of VLCMFAs beyond that of a control cell, seed or plant lacking the heterologous FAE nucleic acid sequence or sequences. The increase may be, for example, by 1.5× or more, 2× or more, 5× or more, or even 10× or more. Specifically, nervonic acid and/or eicosenoic acid levels may be increased by such amounts or even higher. Heterologous expression of the FAE nucleic acid sequence of *T. nudicaulis* and either or both of the FAE nucleic acid sequences of *L. annua* and *C. graeca* is particularly advantageous for increasing levels of nervonic acid in a cell, seed or plant.

Cells that may be transformed with heterologous nucleic acid sequences of the present invention include, for example, yeast cells and plant cells. Species of plants, or cells or seeds of such species, that may be transformed are preferably oilseed plants, for example plants from the family Brassicaceae especially *Arabidopsis, Brassica carinata, Brassica juncea, Brassica napus* or *Camelina sativa*.

Other cells that may be transformed with heterologous nucleic acid sequences of the present invention include, for example borage (*Borago* spp.), Canola, castor (*Ricinus communis*), cocoa bean (*Theobroma cacao*), corn (*Zea mays*), cotton (*Gossypium* spp), *Crambe* spp., *Cuphea* spp., flax (*Linum* spp.), *Lesquerella* spp., *Limnanthes* spp., Linola, nasturtium (*Tropaeolum* spp.), *Oenothera* spp., olive (*Olea* spp.), palm (*Elaeis* spp.), peanut (*Arachis* spp.), rapeseed, safflower (*Carthamus* spp.), soybean (Glycine and *Soja* spp.), sunflower (*Helianthus* spp.), tobacco (*Nicotiana* spp.), *Vernonia* spp., wheat (*Triticum* spp.), barley (*Hordeum* spp.), rice (*Oryza* spp.), oat (*Avena* spp.), sorghum (*Sorghum* spp.), rye (*Secale* spp.) or other members of the Gramineae.

Seed oils having elevated levels of VLCFMA, especially nervonic and eicosenoic acids, may be recovered from transgenic seeds of the present invention by known methods, for example as described in Katavic et al., 2001 and Taylor et al., 2001 for erucic acid and other VLCMFAs.

DETAILED DESCRIPTION OF THE INVENTION

Figure 1:
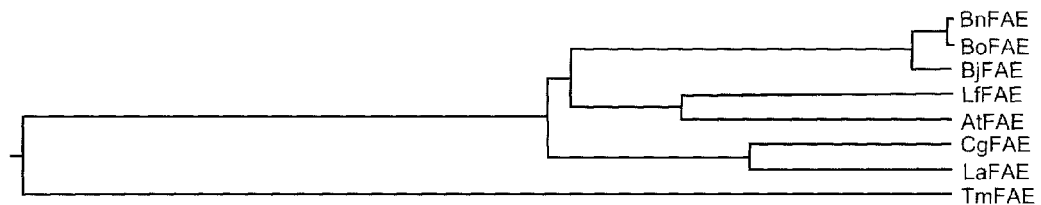
FIG. 1. Dendrogram of the 3-ketoacyl-CoA synthase gene family based on the amino acid sequences. The alignment contains sequence of the *Cardamine graeca* FAE (CgFAE), *Lunaria annua* FAE (LaFAE), *Lesquerella fendleri* FAE (LfFAE), *Brassica juncea* FAE1 (BjFAE), *Brassica oleracea* FAE1 (BoFAE), *Brassica napus* FAE1 (BnFAE), *Arabidopsis thaliana* FAE1 (AtFAE) and *Tropaeolum majus* FAE (TmFAE).

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

The fatty acid elongase (often designated FAE or 3-ketoacyl-CoA synthase (KCS)) is a condensing enzyme and is the first component of the elongation complex involved in synthesis of nervonic acid (24:1 Δ15) and eicosenoic acid (20:1 Δ11) in seeds of *L. annua*, *C. graeca* and *T. nudicaulis*, respectively. Using a polymerase chain reaction method with appropriate primers, genomic DNA clones of a putative embryo FAE were obtained from above mentioned species showing some homology to known plant elongases. Sequence analyses indicated the absence of introns. The *L. annua*, *C. graeca* and *T. nudicaulis* DNA clones contain a 1518, 1521 and 1521 nucleotide ORFs that encode proteins of 506, 507 and 507 amino acids, respectively. To establish the function of the elongase homologs, the coding DNA sequences were introduced into a yeast expression system. The results of yeast expression indicate that both *L. annua* and *C. graeca* FAE genes encode condensing enzymes involved in the biosynthesis of nervonic acid. Yeast expression analyses showed, that *T. nudicaulis* FAE encodes condensing enzyme involved in the biosynthesis of eicosenoic acid. Additionally, reported FAE genes were overexpressed in two heterologous plant backgrounds (*Arabidopsis thaliana* and *Brassica carinata*). The results showed utility for directing or engineering increased synthesis of eicosenoic and nervonic acid in other heterologous organisms/plants.

The invention will now be illustrated by way of non-limiting examples.

EXAMPLE 1

Plant Materials

*Lunaria annua, Cardamine graeca* and *Teesdalia nudicaulis* plants were grown in the greenhouse at the Kristjanson Biotechnology Complex Greenhouses, Saskatoon, under natural light conditions supplemented with high-pressure sodium lamps with a 16 h photoperiod (16 h of light and 8 h of darkness) at 22° C. and a relative humidity of 25 to 30%. Seeds at the mid-developing stage were harvested, frozen in liquid nitrogen and stored at −80° C. until used for genomic DNA isolation. Mature seeds were harvested and used for GC analyses of fatty acid composition of seed lipids.

Heterologous Expression of FAE Polypeptides in Yeast

Yeast cells (line Inv Sc1, Invitrogen) were transformed with pYES2.1/V5-His-TOPO constructs bearing different FAE cDNAs, using the S.c. EasyComp™ Transformation Kit (Invitrogen). As a control in the expression experiments, yeast cells were transformed with pYES2.1/V5-His-TOPO plasmid-only. Transformants were selected by growth on synthetic complete medium lacking uracil (SC-ura) supplemented with 2% glucose. The colonies were transferred into liquid SC-ura medium with 2% glucose and grown at 28° C. overnight. For expression studies the overnight cultures were used to inoculate 25 ml of SC-ura supplemented with 2% galactose to give an initial $OD_{600}$ of 0.2. The cultures were subsequently grown overnight at 20° C. or 28° C. to $OD_{600}$ of 1.4 AU and used for biochemical analyses.

Yeast Protein Preparations and Elongase Assays

Yeast homogenates were prepared essentially according to Ghanevati and Jaworski (16). Cells were harvested and washed with 10 ml of ice-cold isolation buffer consisting of 80 mM HEPES-NaOH, pH 7.2, 5 mM EGTA, 5 mM EDTA, 10 mM KCl, 320 mM sucrose, 2 mM dithiothreitol, pelleted and resuspended in 500 µl of isolation buffer. Cells were broken using three 60-s pulses with MiniBeadbeater™ (Biospec product, Bartlesville, Okla., USA) using 0.5-mm glass beads. The homogenate was collected and briefly centrifuged to remove unbroken cells. Protein concentration was determined using the Bradford method (17). Fatty acid elongase activity of the yeast homogenates was assayed essentially as described by Katavic et al. (18) The assay mixture consisted of 80 mM HEPES-NaOH, pH 7.2; 1 mM ATP; 1 mM CoA-SH; 0.5 mM NADH; 0.5 mM NADPH; 2 mM $MgCl_2$; 1 mM malonyl-CoA; 18 µM [$1-^{14}C$] oleoyl-CoA (0.37 GBq $mol^{-1}$) in a final volume of 500 µL. The reaction was started by the addition of 0.5 mg of protein and incubated at 30° C. for 1 hour. Reactions were stopped by adding 3 mL of 100 g $L^{-1}$ KOH in methanol. Fatty acid methyl esters were prepared and quantified by radio-HPLC as described by Katavic et al. (14, 18).

Lipid Analyses

The yeast cells were grown in 50 ml SC-ura medium supplemented with 2% galactose. The cultures were grown overnight at 28° C. to $OD_{600}$ of 1.4 AU, the cells were spun to form a pellet and used in biochemical analyses. Cell pellets were saponified in methanolic-KOH (10% KOH, 5% $H_2O$ in methanol) for 2 h at 80° C. After saponification, samples were cooled on ice and then washed with hexane to remove non-saponifiable material. The remaining aqueous phase was acidified with 6N HCl. Free fatty acids (FFAs) were extracted in hexane, the solvent removed under a stream of $N_2$, and FFAs were transmethylated in 3N methanolic HCl for 2 h at 80° C. Fatty acid methyl esters (FAMEs) were extracted in hexane, the solvent removed under a $N_2$ stream and the residue was dissolved in hexane for gas-chromatography (GC) under the conditions described previously (18).

The total fatty acid content and acyl composition of *L. annua* and *C. graeca* seed lipids was determined by GC of the FAMEs with 17:0 FAME as an internal standard as described previously (19).

Isolation of FAE Genomic DNA by a PCR Approach

Primers were designed based on the sequence homology among plant fatty acid elongase genes. A 50 µl PCR reaction contained genomic DNA isolated from *L. annua* plant or *C. graeca* developing seed as template with:

```
forward primer for L. annua LA-F1 (SEQ ID NO: 1):
(5'-ATGACGTCCATTAACGTAAAGCTCCTTTACCATTACGTC-3')
and reverse primer for L. annua LA-R1 (SEQ ID NO: 2):
(5'-TTAGGACCGACCGTTTTGGGCACGAGTCTCTG-3')
or forward primer for C. graeca  GC-F1 (SEQ ID NO: 3):
(5'-ATGACGTCCATTAACGTAAAGCTCC-3')
and reverse primer for C. graeca  GC-R1 (SEQ ID NO: 4):
(5'TTAGGACCGACCGTTTTGGGC-3')
``` with Taq DNA Polymerase (Amersham) under standard conditions. Elongase sequences were amplified in a thermalcycler during 30 cycles of the following program: 94° C. for 30 sec, 60° C. for 30 sec and 72° C. for 1 min. The sequence was subsequently cloned into the pYES2.1 expression vector (Invitrogen).

The coding region of *L. annua* or *C. graeca* FAE's in the pYES2.1/V5-His-TOPO plasmid were transformed into *Saccharomyces cerevisiae* strain Inv Sc1 (Invitrogen) using the S.c. EasyComp™ transformation kit (Invitrogen). Yeast cells transformed with pYES2.1/V5-His-TOPO vector only were used as a control. Transformed yeast were selected on minimal agar plates lacking uracil. Transformants were first grown in SC-U (synthetic complete minus uracil) medium at 28° C. overnight, washed and suspended in galactose induction medium (SC-U medium containing 2% galactose) and grown at 28° C. for 2 days.

Sequence Handling

Sequence analyses were performed using Lasergene software (DNAStar™). Sequence similarity searches and other analyses were performed using BLASTN, BLASTX (20) and PSORT (21) program.

Plant Transformation

*Arabidopsis* (*A. thaliana* ecotype Wassilewskija) were transformed by vacuum infiltration according to the method of Clough and Bent (22). Transgenic plants were selected and analyzed essentially as described by Mietkiewska et al. (23).

*Brassica carinata* plants were transformed using the protocol described by Babic et. al. (24). Shoots that rooted in the presence of 25 mg/L kanamycin were considered to be transgenic. Transgenic plants were transferred to soil and grown in a growth chamber. $T_1$ seed from self-pollinated plants were harvested and subjected to biochemical analysis performed as described by Mietkiewska et al. (23)

EXAMPLE 2

Composition of *L. annua* or *C. graeca* Seed Lipids

The acyl composition of the TAG fraction of *L. annua* and *C. graeca* had highly enriched proportions of very long chain monounsaturated fatty acids (VLCMFAs) with 36% erucic acid (22:1 Δ13) and 25% nervonic acid (24:1 Δ15) in *L. annua* plant seed oil while *C. graeca* had 10% erucic acid and 43% nervonic acid in the seed oil.

EXAMPLE 3

Isolation of *L. annua* and *C. graeca* FAE Homologs

Based on sequence homology among plant fatty acid elongase genes, full-length clones were amplified by PCR as in Example 1. The nucleotide sequences had open reading frame of 1518 and 1521 bp, respectively (SEQ ID NO: 5 and 6).

The analysis of the nucleotide sequence corresponding to *L. annua* and *C. graeca* FAE genomic clones revealed the absence of intron sequences. A similar absence of introns was observed in homologs from *A. thaliana* FAE1, rapeseed CE7 and CE8 and high and low erucic lines of *B. oleracea, B. rapa,* canola *B. napus* cv Westar and HEAR *B. napus* cv Hero and *T. majus*.

The *L. annua* and *C. graeca* FAE nucleotide sequences encode polypeptides of 506 and 507 amino acids (SEQ ID NO: 7 and 8), respectively. The *L. annua* and *C. graeca* FAE protein were predicted to have a molecular mass of 56.06 kD and 56.46 kD, respectively.

*L. annua* plant FAE polypeptide is most closely related to *B. juncea* and *A. thaliana* FAE1 with 85% amino acid identity, showing 84% identity with other *Brassica* FAE1 polypeptides (*B. oleracea, B. rapa, B. napus*) while homology of the *L. annua* plant FAE to *Lesquerella fendleri* FAE polypeptide was on the level of 76% amino acid identity (FIG. 1).

*C. graeca* FAE protein showed the highest amino acid sequence identity with *A. thaliana* FAE1 (81%), 79% identity with *B. juncea, B. napus, B. rapa* and *B. oleracea* FAE1 proteins and a 75% amino acid identity with the *L. fendleri* FAE polypeptide (FIG. 1). Previously isolated *Tropaeolum majus* FAE showed 54% and 52.5% identity with the *L. annua* and *C. graeca* FAE polypeptides, respectively. The *L. annua* and *C. graeca* FAE polypeptides showed 85.6% identity to each other. These homologs all exhibit the capability to elongate monounsaturated fatty acids to produce monounsaturated VLCFAs. However, only the FAEs from *Lunaria* and *Cardamine* show a strong preference for producing nervonic acid.

Figure 2A:
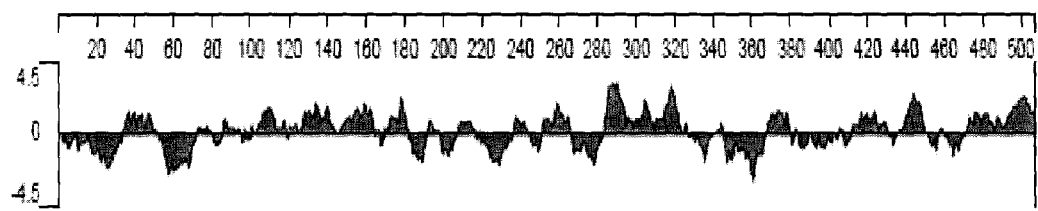
FIG. 2. Hydropathy analysis of Lunaria annua FAE. A) Hydropathy plot of FAE indicating the presence of several hydrophobic regions. B) Schematic representation of the putative transmembrane domains of *L. annua* FAE amino-acid sequence as predicted by TMAP analysis (21). Numbers shown in the boxes correspond to the residues of each domain in FAE.
Figure 2B:
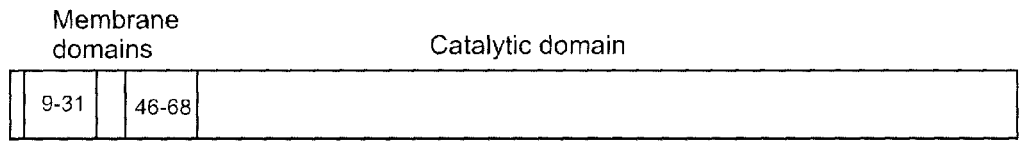
Figure 3A:
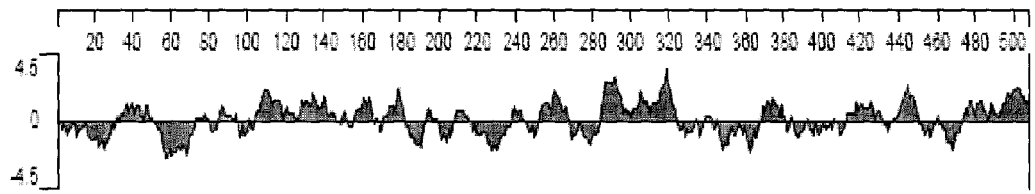
FIG. 3. Hydropathy analysis of *Cardamine graeca* FAE. A) Hydropathy plot of FAE indicating the presence of several hydrophobic regions. B) Schematic representation of the putative transmembrane domains of *C. graeca* FAE amino-acid sequence as predicted by TMAP analysis [Persson, Argos 1994]. Numbers shown in the boxes correspond to the residues of each domain in FAE.
Figure 3B:
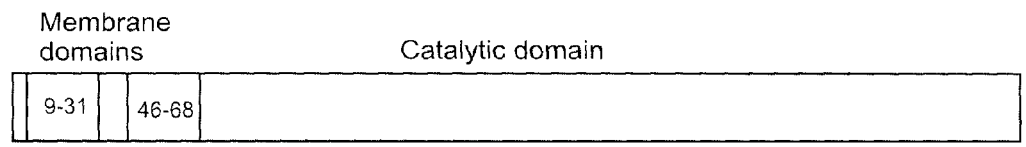

A hydropathy analysis (Kyte-Doolittle) of the amino acid sequence of the *L. annua* and *C. graeca* FAE polypeptides revealed several hydrophobic domains (FIGS. 2A and 3A). Protein analyses with the TMAP algorithm (21) predicted two N-terminal transmembrane domains in *L. annua* FAE, the first corresponding to amino acid residues 10 to 29 and the second domain spanning residues 50 to 72 (FIG. 2B). Similarly, two N-terminal transmembrane domains were predicted in *C. graeca* FAE, the first corresponding to amino acid residues 9 to 31 and the second domain spanning residues 46 to 68 (FIG. 3B).

EXAMPLE 4

Heterologous Expression of *L. annua* and *C. graeca* FAE in Yeast

Figure 4:
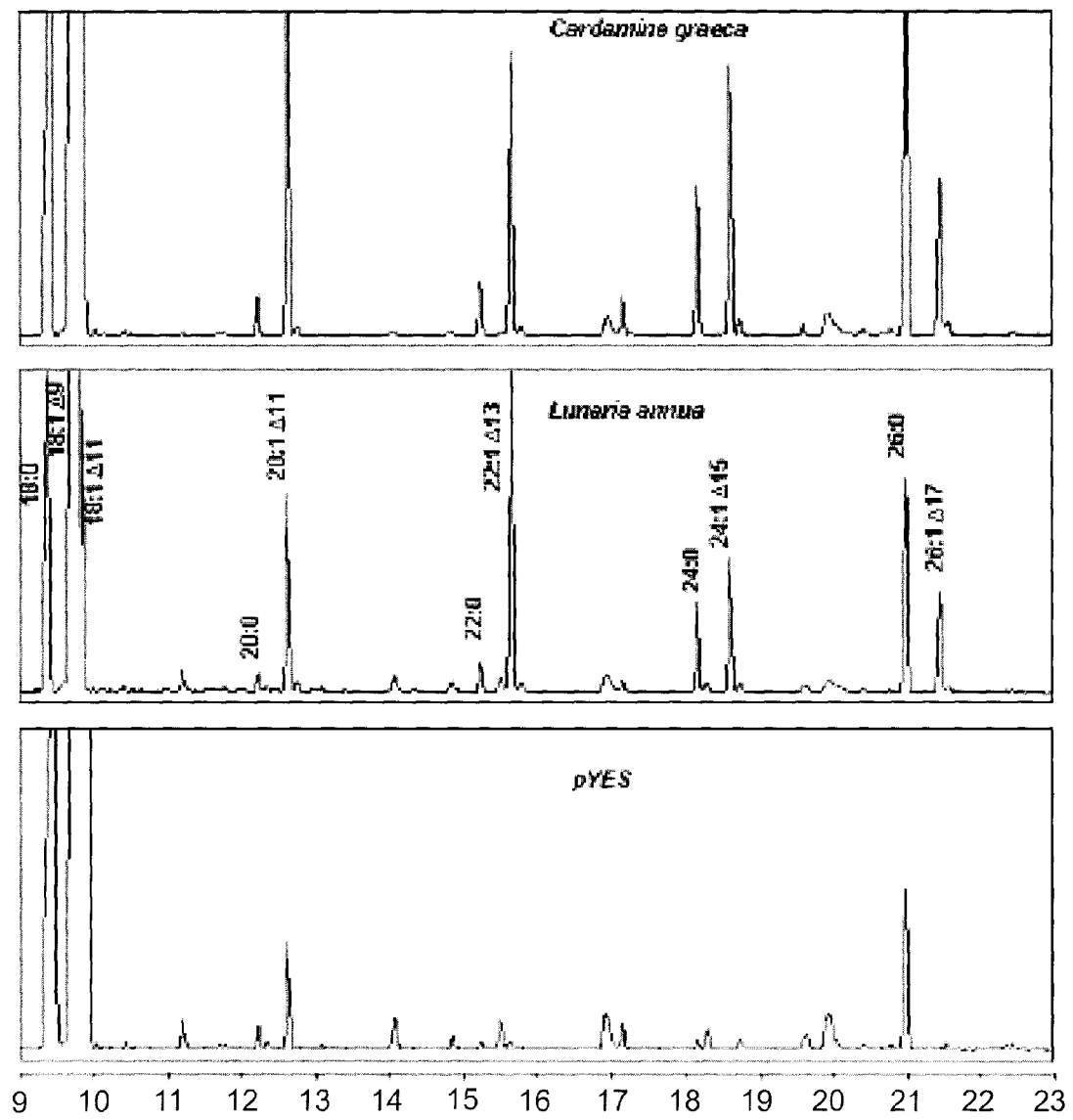
FIG. 4. GC chromatographs showing fatty acid profiles of yeast cells transformed with *Lunaria annua* or *Cardamine graeca* FAE genes. As a negative control pYES2.1/V5-His-TOPO plasmid (pYES) were used.

To study the function of the protein encoded by the *L. annua* and *C. graeca* FAE, the coding region of each gene was linked individually to the galactose-inducible GAL1 promoter in the expression vector pYES2.1 and transformed into yeast. The GC analyses of fatty acid profiles in yeast cells upon FAE expression revealed the presence of saturated and monounsaturated very long chain fatty acids that are not normally present in yeast, with distinct peaks corresponding to nervonic acid (24:1 Δ15; FIG. 4).

Figure 5A:
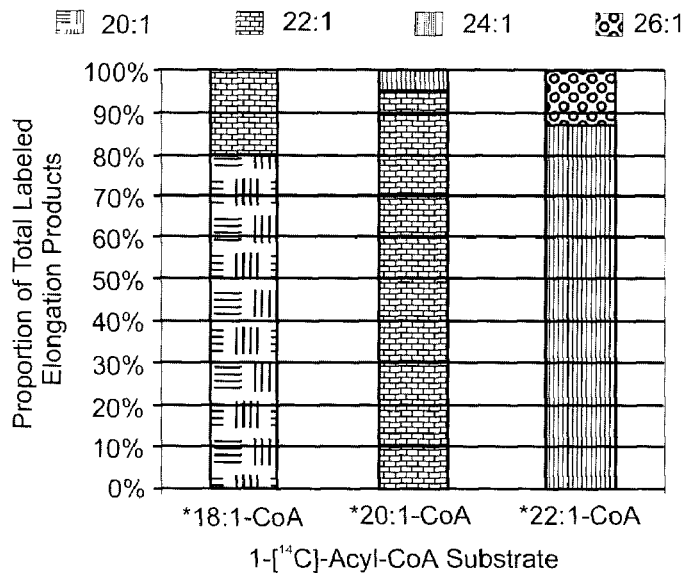
FIG. 5. Elongase activity assayed in lysates from yeast cells upon expression of A) *Lunnaria annua* FAE, and B) *Cardamine graeca* FAE.
Figure 5B:
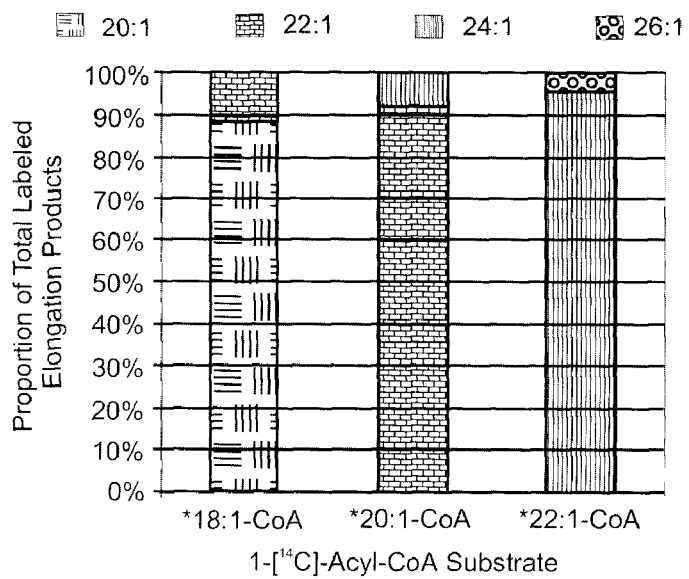

Elongase Activity in Yeast Cells upon Expression of *L. annua* and *C. greaca* FAE Clones To determine elongase activity in yeast cells expressing FAE genes from *L. annua* plant and *C. graeca* elongase activity assays were performed using yeast homogenates prepared from induced yeast cells and a range of $[1-^{14}C]$ acyl CoAs and malonycl-CoA as substrates. The elongase activity assays confirmed the ability of *L. annua* and *C. graeca* FAE enzymes to synthesize nervonic acid (FIG. 5). For both FAEs, the 22:1-CoA was a preferred substrate for the synthesis of nervonic acid in yeast cells. When we compared the elongase activity with 22:1 CoA, higher activity was found for *C. graeca* FAE (92% of 24:1) than for *L. annua* FAE (87% of 24:1).

EXAMPLE 5

Heterologous Expression of the *L. annua* and *C. graeca* FAE in *Arabidopsis*

The coding regions of the *L. annua* and *C. graeca* FAEs were amplified by polymerase chain reaction with primers: forward LA/CG-F2 (SEQ ID NO: 9): 5'-gctctagaAT-GACGTCCATTAACGTAA-3' (lower case shows restriction site for XbaI) and reverse LA/CG-R2 (SEQ ID NO: 10): 5'-ggggtaccTTAGGACCGACCGTTT-3' (lower case shows restriction site for KpnI) and subsequently cloned behind the napin promoter in respective sites of pSE vector (25).

The final binary vectors (napin/*L. annua* FAE or napin/*C. graeca* FAE) were electroporated into *Agrobacterium tumefaciens* cells strain GV3101 containing helper plasmid pMP90 (26). Plasmid integrity was verified by DNA sequencing following its re-isolation from *A. tumefaciens* and transformation into *E. coli*.

Subsequently they were used to transform *A. thaliana* plants by the vacuum infiltration method (22).

From vacuum-infiltration experiments, 36 kanamycin-resistant $T_1$ plants from each transformation were selected. The $T_2$ progeny were collected individually from each plant and the fatty acid composition determined. Results from the best 15 *Arabidopsis* $T_2$ transgenic lines are shown in Table 1. Results in Table 1 represent the average±SD of measurements using 200 seeds from 15 independent *Arabidopsis* transgenic lines. Constructs: RD=Control (plasmid only) transgenic seeds; LA=Napin: *L. annua* FAE; CG=Napin: *C. graeca* FAE transgenic seeds.

TABLE 1

Fatty Acid Composition of Transgenic *Arabidopsis* $T_2$ Seed Oils

| Fatty Acid Composition | | Construct | | |
|---|---|---|---|---|
| | | RD | LA | CG |
| 20:1 | % (w/w) | 18.61 ± 0.25 | 6.79 ± 0.81 | 6.96 ± 0.62 |
| | range | 18.29-18.89 | 5.30-8.07 | 5.89-8.02 |
| | % increase[a] | — | — | — |
| 22:0 | % (w/w) | 0.30 ± 0.00 | 1.23 ± 0.09 | 1.03 ± 0.08 |
| | range | 0.30-0.31 | 1.06-1.35 | 0.89-1.17 |
| | % increase[a] | — | 310.00 | 243.33 |
| 22:1 | % (w/w) | 1.99 ± 0.24 | 13.76 ± 0.77 | 6.50 ± 0.28 |
| | range | 1.66-2.21 | 12.59-15.18 | 6.11-6.90 |
| | % increase[a] | — | 591.46 | 226.63 |

TABLE 1-continued

Fatty Acid Composition of Transgenic *Arabidopsis* $T_2$ Seed Oils

| Fatty Acid Composition | | Construct | | |
|---|---|---|---|---|
| | | RD | LA | CG |
| 24:0 | % (w/w) | 0.20 ± 0.04 | 1.02 ± 0.11 | 1.82 ± 0.25 |
| | range | 0.16-0.25 | 0.86-1.18 | 1.31-2.24 |
| | % increase[a] | — | 410.00 | 810.00 |
| 24:1 | % (w/w) | 0.19 ± 0.01 | 4.25 ± 0.55 | 8.48 ± 0.63 |
| | range | 0.17-0.20 | 3.28-5.06 | 7.52-9.19 |
| | % increase[a] | — | 2136.84 | 4363.16 |
| 26:1 | % (w/w) | 0.10 ± 0.05 | 0.22 ± 0.03 | 0.39 ± 0.04 |
| | range | 0.05-0.17 | 0.18-0.30 | 0.33-0.45 |
| | % increase[a] | — | 120.00 | 290.00 |
| LCFA | % (w/w) | 70.71 ± 0.47 | 68.61 ± 1.14 | 69.67 ± 0.80 |
| | range | 70.05-71.12 | 66.36-70.56 | 68.28-71.08 |
| | % increase[a] | — | — | — |
| VLCFA | % (w/w) | 29.29 ± 0.47 | 31.39 ± 1.14 | 30.33 ± 0.80 |
| | range | 29.04-29.95 | 29.44-33.64 | 28.92-31.72 |
| | % increase[a] | — | — | — |

[a]Relative to value for seeds from RD: the *Arabidopsis* control (plasmid only) plants, set at 100%.

Significant changes in fatty acid composition in comparison to the control line (empty vector) were found. Seed specific expression of *L. annua* FAE resulted in increased proportions of erucic and nervonic acid at the expense of eicosenoic acid. One average, the level of erucic and nervonic acid was increased from 1.99 and 0.19% in the control line up to 13.76 and 4.25% in the $T_2$ transgenic seeds, respectively.

Seed specific expression of *C. graeca* FAE resulted in higher accumulation of nervonic acid (24:1 Δ15). On average the level of nervonic acid increased from 0.19% in the control line up to 8.48% in the $T_2$ transgenic seeds. There was also a significant increase in level of erucic acid (22:1 Δ13) from 1.99% in the control line up to 6.50% in the transgenic lines (Table 1).

Figure 6A:
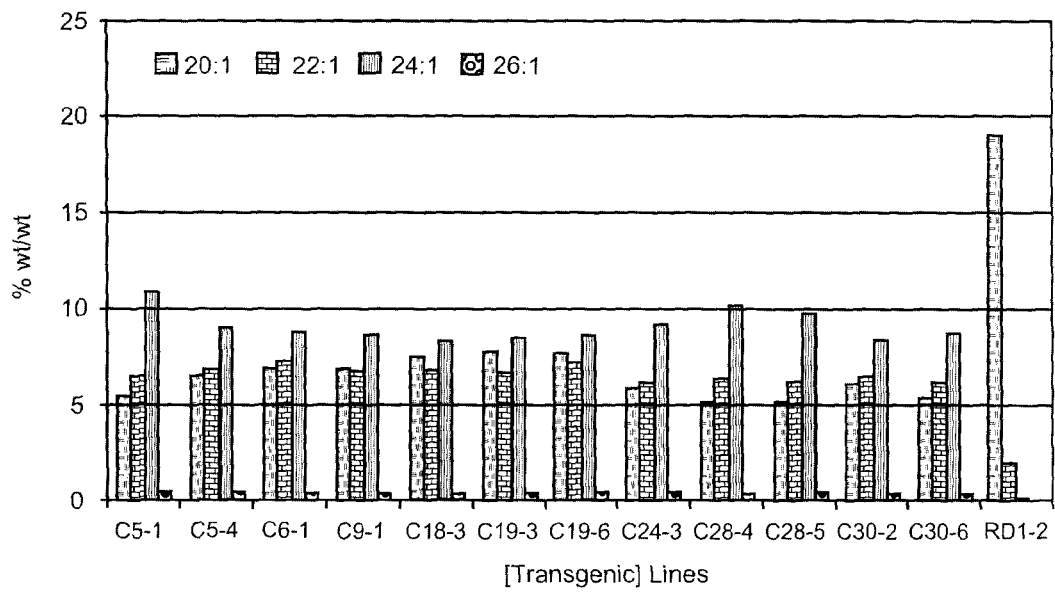
FIG. 6. Fatty acid composition of transgenic *Arabidopsis* seeds. A) Proportions of 20:1 Δ11, 22:1 Δ13, 24:1 Δ15, and 26:1 Δ17 in seed oils from plasmid-only transgenic control line (RD-1-2), and the 12 best *A. thaliana* $T_3$ homozygous transgenic lines expressing the *C. graeca* FAE (C) gene under control of the napin promoter. B) Proportions of 22:0 and 24:0 in seed oils from plasmid only transgenic control line (RD-1-2), and the 12 best *A. thaliana* $T_3$ homozygous transgenic lines expressing the *C. graeca* FAE gene (C) under control of the napin promoter. The values are determined on a 200 seed lot.
Figure 6B:
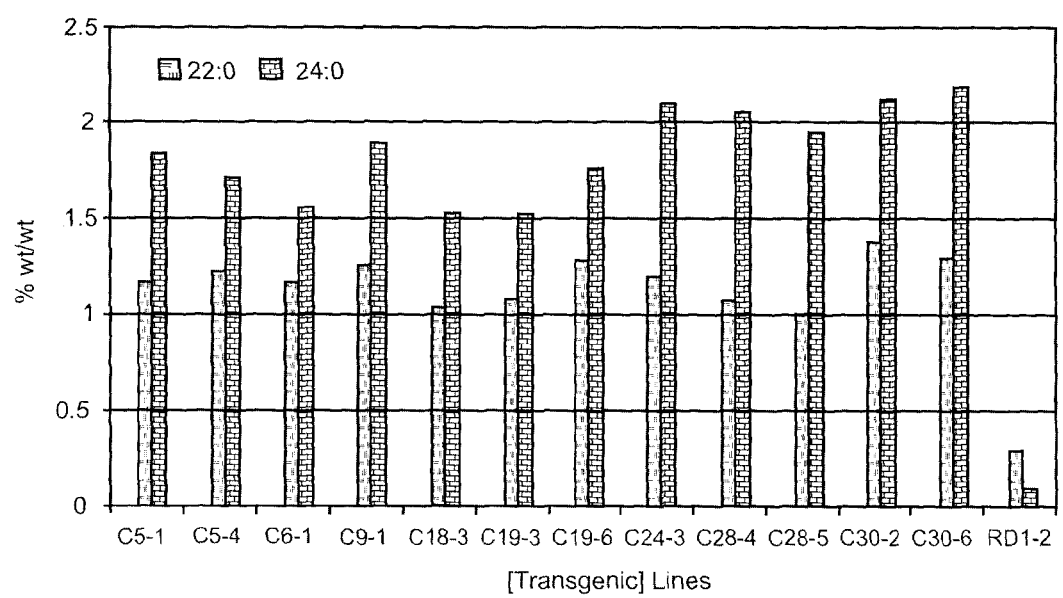

Homozygous $T_3$ lines were analyzed to examine the range of VLCFA proportional re-distribution induced by expression of the *C. graeca* FAE gene. The 12 best $T_3$ lines are shown in FIGS. 6A and B. The nervonic acid content was increased by up to 63 fold in lines: C28-4, C28-5. Small increase in the proportions of 26:1 Δ17 was also observed. There was also a relatively significant increase in the proportions of the saturated VLCFAs, 22:0 and 24:0.

Figure 7A:
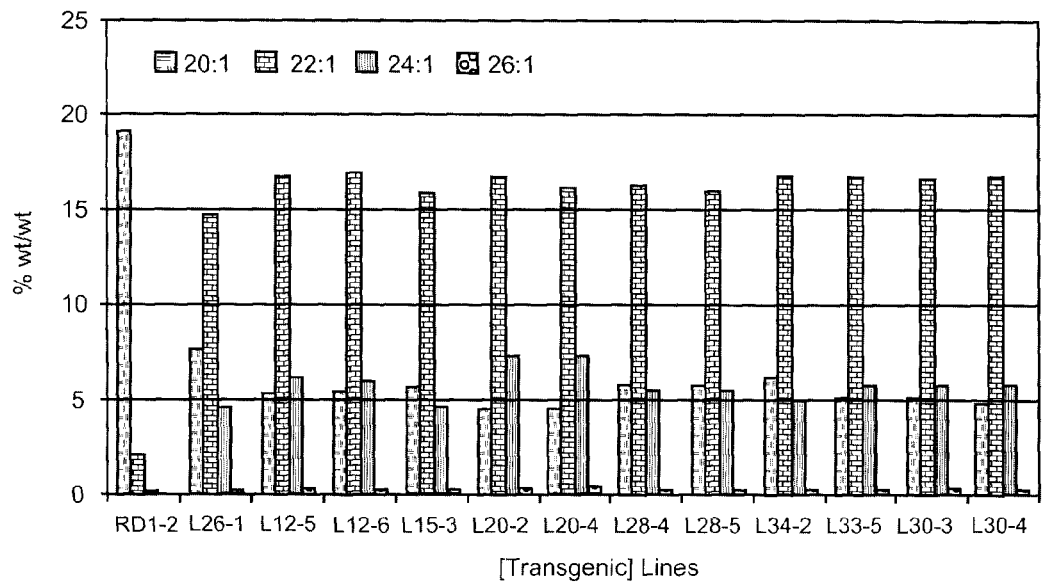
FIG. 7. Fatty acid composition of FAE transgenic *Arabidopsis* seeds. A) Proportions of 20:1 Δ11, 22:1 Δ13, 24:1 Δ15, and 26:1 Δ17 in seed oils from plasmid-only transgenic control line (RD-1-2), and the 12 best *A. thaliana* $T_3$ homozygous transgenic lines expressing the *L. annua* FAE gene (L) under control of the napin promoter. B) Proportions of 22:0 and 24:0 in seed oils from plasmid only transgenic control line (RD-1-2), and the 12 best *A. thaliana* $T_3$ homozygous transgenic lines expressing the *L. annua* FAE gene (L) under control of the napin promoter. The values are determined on a 200 seed lot.
Figure 7B:
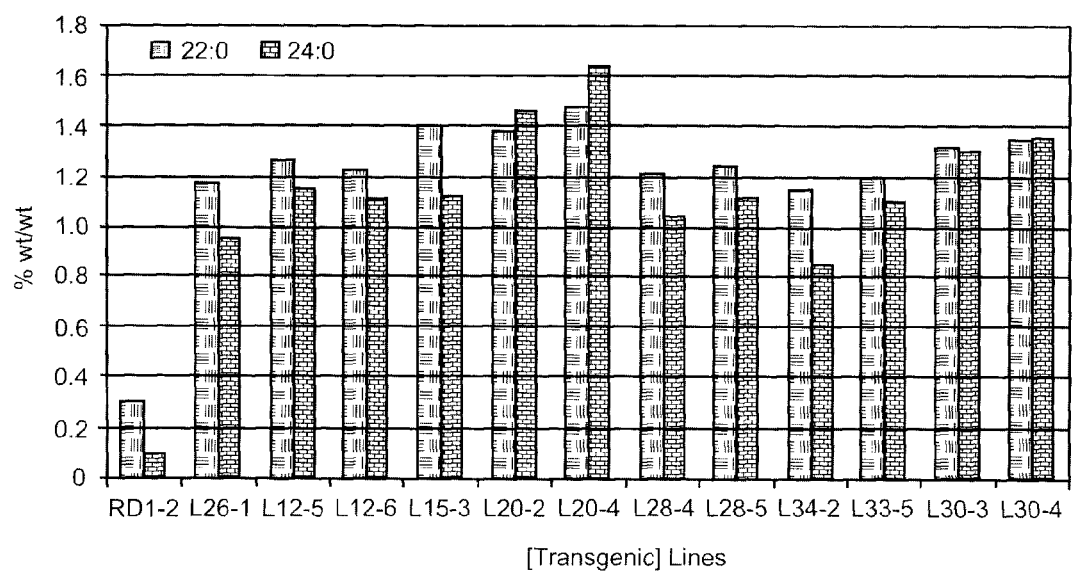

The 12 best $T_3$ homozygous lines expressing *L. annua* FAE are shown in FIGS. 7A and 7B. The nervonic acid content was increased by up to 30-40 fold in lines: L12-5, L20-2 and L20-4. The level of erucic acid was increased from 1.98% in the control line to as high as 16.8% in the best transgenic lines. There was also a relatively significant increase in the proportions of the saturated VLCFAs, 22:0 and 24:0.

EXAMPLE 6

Heterologous Expression of the *L. annua* and *C. graeca* FAE in HEAR Brassicaceae—e.g. *B. carinata*

The binary vectors carrying *L. annua* and *C. graeca* FAE under the control of the napin promoter were used to transform *B. carinata* plants using the method of Babic et al. (24). Shoots that rooted in the presence of 25 mg/L kanamycin were considered transgenic. Transgenic plants were transferred to soil and grown in a growth chamber. $T_1$ seed from self pollinated plants were harvested and subjected to biochemical analysis performed as described by Mietkiewska et al., (23). Results from the best 15 $T_1$ transgenic *B. carinata* lines are shown in Table 2. Results in Table 2 represent the average±SD of measurements using 12 seeds from 15 independent *B. carinata* transgenic lines. Constructs: CK=Control (plasmid only) transgenic seeds; LA=Napin: *L. annua* FAE; CG=Napin: *C. graeca* FAE transgenic seeds.

TABLE 2

Fatty Acid Composition of Transgenic *Brassica Carinata* $T_1$ Seed Oils

| Fatty Acid Composition | | Construct | | |
|---|---|---|---|---|
| | | CK | LA | CG |
| 18:0 | % (w/w) | 0.69 ± 0.02 | 0.61 ± 0.11 | 0.38 ± 0.05 |
| | range | 0.66-0.72 | 0.47-0.78 | 0.28-0.47 |
| | % increase[a] | — | — | — |
| 20:1 | % (w/w) | 4.09 ± 0.30 | 2.00 ± 0.57 | 1.44 ± 0.63 |
| | range | 3.73-4.47 | 1.13-3.14 | 0.47-2.64 |
| | % increase[a] | — | — | — |
| 22:0 | % (w/w) | 0.49 ± 0.00 | 0.62 ± 0.14 | 0.34 ± 0.05 |
| | range | 0.49-0.49 | 0.42-0.81 | 0.24-0.45 |
| | % increase[a] | — | — | — |
| 22:1 | % (w/w) | 35.80 ± 1.90 | 29.01 ± 2.56 | 9.81 ± 2.51 |
| | range | 33.13-37.36 | 23.25-33.54 | 5.43-15.19 |
| | % increase[a] | — | — | — |
| 24:0 | % (w/w) | 0.60 ± 0.03 | 1.46 ± 0.22 | 2.02 ± 0.38 |
| | range | 0.56-0.62 | 1.18-1.88 | 1.56-3.02 |
| | % increase[a] | — | 143.33 | 236.67 |
| 24:1 | % (w/w) | 2.76 ± 0.11 | 19.50 ± 3.79 | 38.03 ± 2.87 |
| | range | 2.63-2.91 | 13.07-25.86 | 32.28-43.52 |
| | % increase[a] | — | 606.52 | 1277.90 |
| LCFA | % (w/w) | 50.34 ± 1.68 | 42.33 ± 3.28 | 37.86 ± 2.60 |
| | range | 48.97-52.71 | 37.51-48.06 | 34.61-45.07 |
| | % increase[a] | — | — | — |
| VLCFA | % (w/w) | 49.66 ± 1.68 | 57.67 ± 3.28 | 62.14 ± 2.60 |
| | range | 47.29-51.03 | 51.94-62.49 | 54.93-65.39 |
| | % increase[a] | — | — | — |

[a]Relative to value for seeds from CK: the plasmid only control plants set at 100%.

Seed specific expression of *C. graeca* FAE resulted in higher accumulation of nervonic acid compared to plants overexpressing *L. annua* FAE. On average the proportion of nervonic acid in $T_1$ segregating seeds increased from 2.76% in control line to as high as 38.03% in the plants carrying *C. graeca* FAE and 19.5% in the plants transformed with *L. annua* FAE. Nervonic acid was synthesized at the expense of 22:1 and 20:1 fatty acids.

Figure 8A:
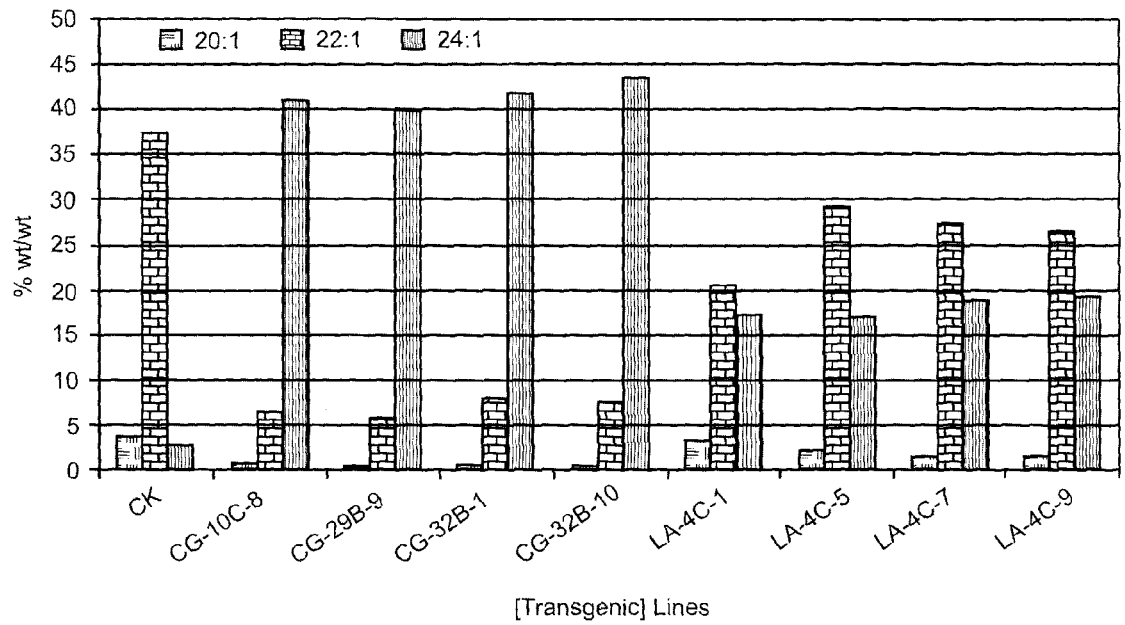
FIG. 8. Fatty acid composition of transgenic *Brassica carinata* seeds. A) Proportions of 20:1 Δ11, 22:1 Δ13, and 24:1 Δ15 in seed oils from plasmid-only transgenic control line (CK), and the 4 best *B. carinata* $T_2$ transgenic lines expressing the *C. graeca* FAE gene (CG) and the 4 best *B. carinata* $T_2$ transgenic lines expressing the *L. annua* FAE gene (LA) under control of the napin promoter. B) Proportions of 22:0 and 24:0 in seed oils from plasmid only transgenic control line (CK), and the 4 best *B. carinata* $T_2$ transgenic lines expressing the *C. graeca* FAE gene (CG) and the 4 best *B. carinata* $T_2$ transgenic lines expressing the *L. annua* FAE gene (LA) under control of the napin promoter. The values are determined on a 12 seed lot and performed in triplicate.
Figure 8B:
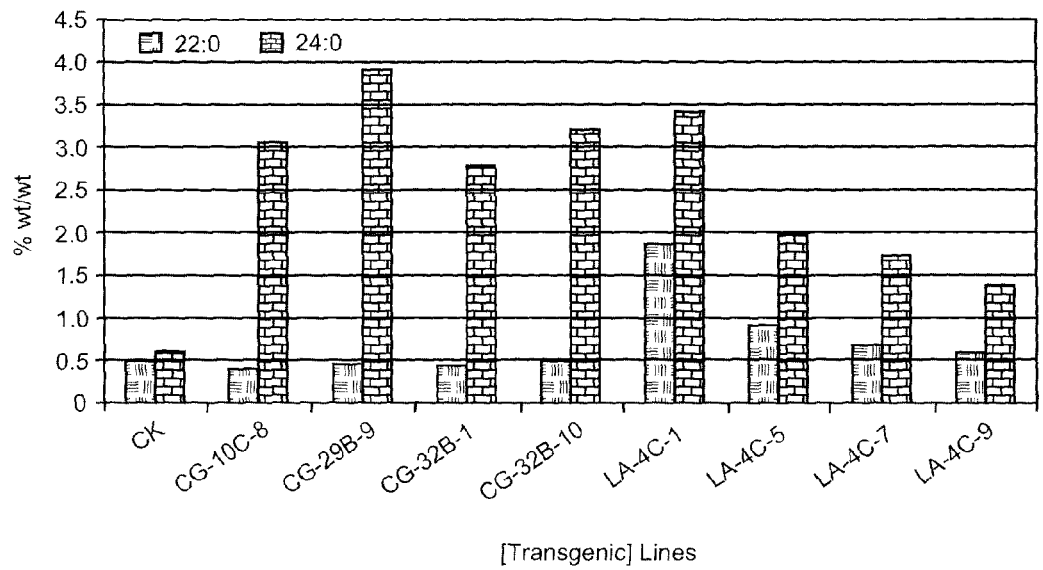

The best transgenic *B. carinata* $T_1$ seeds were selected and subsequently grown in the greenhouse to the next generation. The seeds of $T_2$ lines were analyzed by GC to examine the range of VLCFAs proportional re-distribution induced by expression of the *C. graeca* or *L. annua* FAE genes. Results from the 4 best $T_2$ lines are shown in FIGS. 8A and 8B. Higher accumulation of nervonic acid was found for *B. carinata* lines transformed with *C. graeca* FAE (CG lines) compared to plants carrying *L. annua* FAE (LA lines). The nervonic acid content was increased by up to 13-14 fold in the best CG lines compared to the control line, while in the best LA lines the level of nervonic acid increased up to 4-5 folds. Increased level of nervonic acid was correlated with concomitant reduction in the proportion of its corresponding elongase primer: mainly 22:1 Δ13 and 20:1 Δ11. There was also a relatively significant increase in the proportions of the saturated VLCFAs, 24:0. Of great importance, as indicated in FIG. 8A for the *C. graeca* transformants, the proportion of erucic acid fell from 37% to well below 10%, typically 5-8%, which, according to industry sources and the intellectual property office at the University of Guelph, is the much preferred level of erucic acid for pharmaceutical/nutraceutical uses of the seed oil. Too high a level of erucic acid is deemed undesirable for human or animal consumption due to its potentially toxic properties.

EXAMPLE 7

Acyl Composition of T. nudicaulis Seed Lipids

The acyl composition of the TAG fraction of T. nudicaulis seeds had highly enriched proportions of very long chain monounsaturated fatty acids (VLCMFAs) with 47.5% of eicosenoic acid (20:1 Δ11).

Cloning of T. nudicaulis 3-Ketoacyl-CoA Synthase (FAE) and Heterologous Expression in Yeast Based on FAE1 sequences from Arabidopsis thaliana and Brassica napus, the forward primer TN-F1 (SEQ ID NO: 11): (5'-GCAATGACGTCCGTTAACGTTAAG-3') and the reverse primer TN-R1 (SEQ ID NO: 12): (5'-GGACCGAC-CGTTTTGGAC-3') were designed and used to isolate the T. nudicaulis FAE coding region. Genomic DNA isolated from leaves according to urea-phenol extraction method (27), was used as a template for PCR amplification with Vent DNA polymerase (New England Biolabs) in a thermocycler during 30 cycles of the following program: 94° C. for 30 sec, 52° C. for 30 sec, and 72° C. for 2 min. A 1.5-kB PCR product was cloned into pYES2.1/V5-His-TOPO expression vector and subsequently sequenced. The T. nudicaulis FAE in pYES2.1/V5-His-TOPO was transformed into Saccharomyces cerevisiae strain Inv Sc1 (Invitrogen) using the S.c. EasyComp™ transformation kit (Invitrogen). Yeast cells transformed with pYES2.1/V5-His-TOPO plasmid only were used as a control. The transformants were selected and grown as described previously (18, 23). Fatty acid methyl esters (FAMEs) from yeast cultures were extracted and analyzed as described by Katavic et al., (18).

Isolation of T. nudicaulis FAE Homolog

Figure 9:
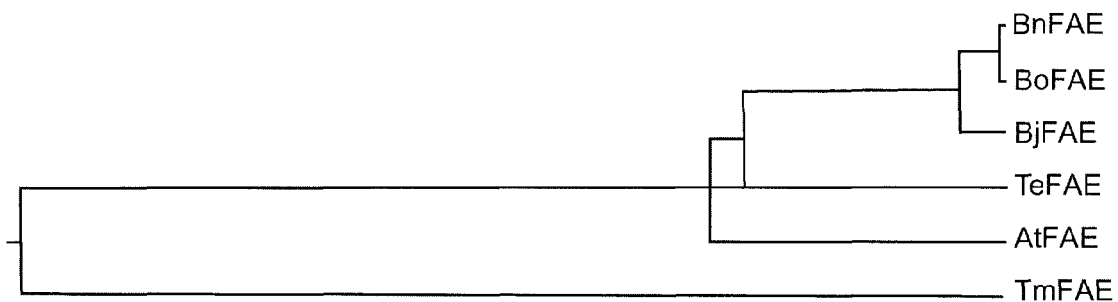
FIG. 9. Dendrogram of the 3-ketoacyl-CoA synthase gene family based on the amino acid sequences. The alignment contains sequence of the *Teesdalia nudicaulis* (TeFAE), *Brassica juncea* FAE1 (BjFAE), *Brassica oleracea* FAE1 (BoFAE), *Brassica napus* FAE1 (BnFAE), *Arabidopsis thaliana* FAE1 (AtFAE) and *Tropaeolum majus* FAE (TmFAE).

Based on the sequence homology among plant fatty acid elongase genes, a coding region of the FAE gene (SEQ ID NO: 13) from T. nudicaulis was isolated. The T. nudicaulis FAE open reading frame of 1521-bp encodes a polypeptide of 507 amino acid (SEQ ID NO: 14) that is most closely related to an FAE1 from Cruciferaceae (FIG. 9): B. juncea (84.6% identity, GenBank #AJ558198), B. olearcea (84.2% identity, GenBank #AF490-460), B. napus (83.8% identity, GenBank #AF490-459). The Arabidopsis FAE1 (GenBank #U29142) polypeptide showed 82% identity with the T. nudicaulis FAE. Previously isolated Tropaeolum majus FAE (GenBank #AY082610) showed 51.5% identity with the T. nudicaulis FAE. The T. nudicaulis FAE protein was predicted to have a molecular mass of 56.2 kD and a theoretical pI value of 9.27.

Figure 10A:
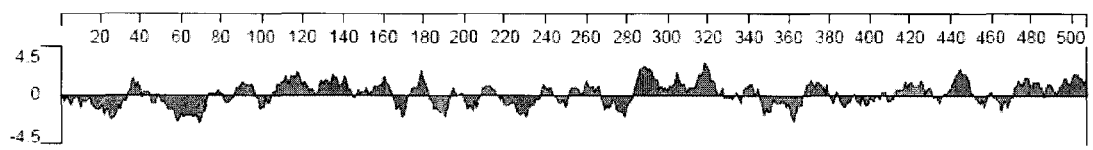
FIG. 10. Hydropathy analysis of *Teesdalia nudicaulis* FAE. A) Hydropathy plot of FAE indicating the presence of several hydrophobic regions. B) Schematic representation of the putative transmembrane domains of *T. nudicaulis* FAE amino-acid sequence as predicted by TMAP analysis [Persson, Argos 1994]. Numbers shown in the boxes correspond to the residues of each domain in FAE.

A hydropathy analysis (Kyte-Doolittle) of the amino acid sequence of the T. nudicaulis FAE revealed several hydrophobic domains (FIG. 10A).

Figure 10B:
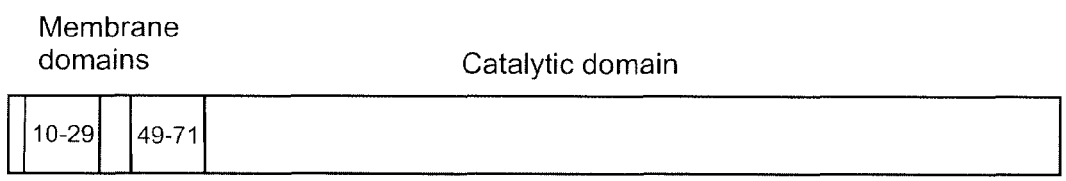

Protein analyses with the TMAP algorithm (21) predicted two N-terminal transmembrane domains, the first corresponding to amino acid residues 10 to 29 and the second domain spanning residues 49 to 71 (FIG. 10B).

EXAMPLE 8

Functional Heterologous Expression of the T. nudicaulis FAE in Yeast Cells

Figure 11:
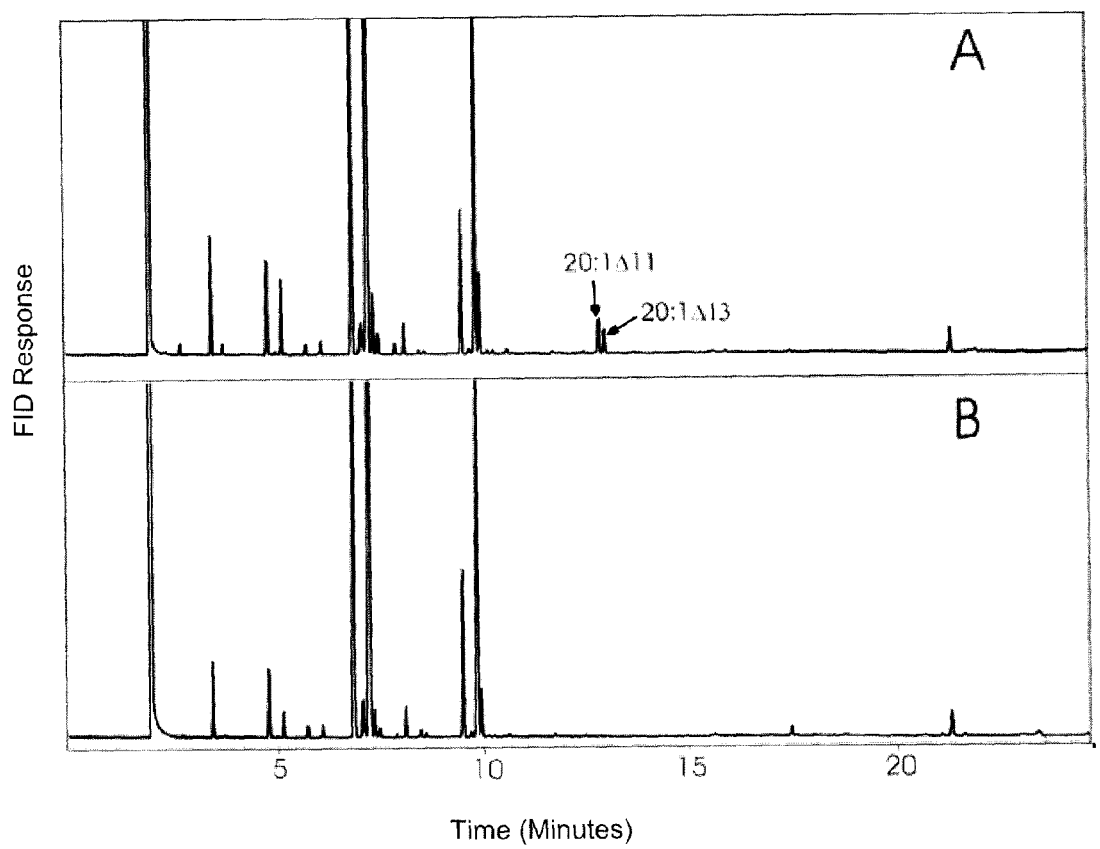
FIG. 11. Expression of *Teesdalia nudicaulis* FAE in yeast cells. A) Yeast cells transformed with pYES 2.1 plasmid containing *Teesdalia* FAE. B) Yeast cells transformed with empty pYES 2.1 plasmid.

To study the function of the protein encoded by the T. nudicaulis FAE, the coding region was linked to the GAL1-inducible promoter in the yeast expression vector pYES2.1/V5-His-TOPO and transformed into S. cerevisiae strain Inv Sc1 yeast cells. As shown in FIG. 11, yeast cells transformed with the plasmid containing the T. nudicaulis FAE open reading frame were found to have an accumulation of 20:1 Δ11, 20:1 Δ13, these are not present in wild-type yeast cells.

Figure 12:
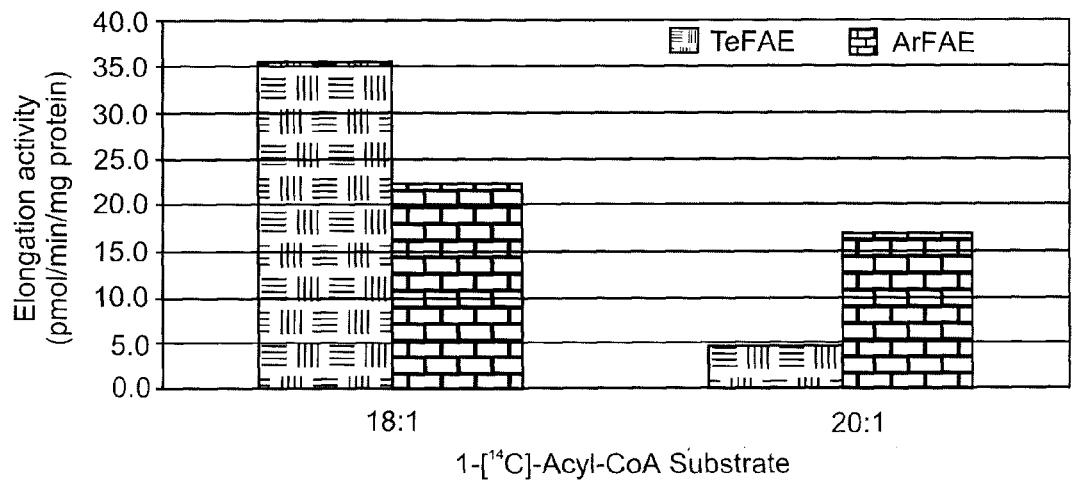
FIG. 12. Elongase activity assayed in yeast cell upon expression with *T. nudicaulis* FAE (TeFAE) and *A. thaliana* FAE1 (ArFAE).

To determine the substrate of preference for T. nudicaulis FAE in yeast cells and compare it with Arabidopsis FAE1, we performed elongase assay with a range of radiolabeled 1-[$^{14}$C]acyl-CoA and malonyl-CoA as substrates. As shown in FIG. 12, T. nudicaulis FAE exhibited higher (35.49 pmol min$^{-1}$ protein) and more specific activity with 18:1-CoA compared to Arabidopsis FAE1 (22.28 pmol min$^{-1}$ protein).

EXAMPLE 9

Heterologous Expression of the T. nudicaulis FAE in Arabidopsis

The coding regions of the T. nudicaulis FAE was amplified by polymerase chain reaction with primers: forward TN-F2 (SEQ ID NO: 15): 5'-tatctagaATGACGTCCGTTAACGT-TAAG-3' (lower case-restriction site for XbaI) and reverse TN-R2 (SEQ ID NO: 16): 5'-atggtaccTTAGGACCGAC-CGTTTTGG-3' (lower case shows restriction site for KpnI enzyme) and subsequently cloned behind the napin promoter in respective sites of pSE vector (24).

The final binary vector (napin/T. nudicaulis FAE) was electroporated into Agrobacterium tumefaciens cells strain GV3101 containing helper plasmid pMP90 (26). Plasmid integrity was verified by DNA sequencing following its re-isolation from A. tumefaciens and transformation into E. coli.

The binary vector was used to transform A. thaliana plants (ecotype Columbia and fae1 mutant line AC56) by the vacuum infiltration method (22) and high erucic B. carinata plants using the method of Babic et al., (24).

Figure 13:
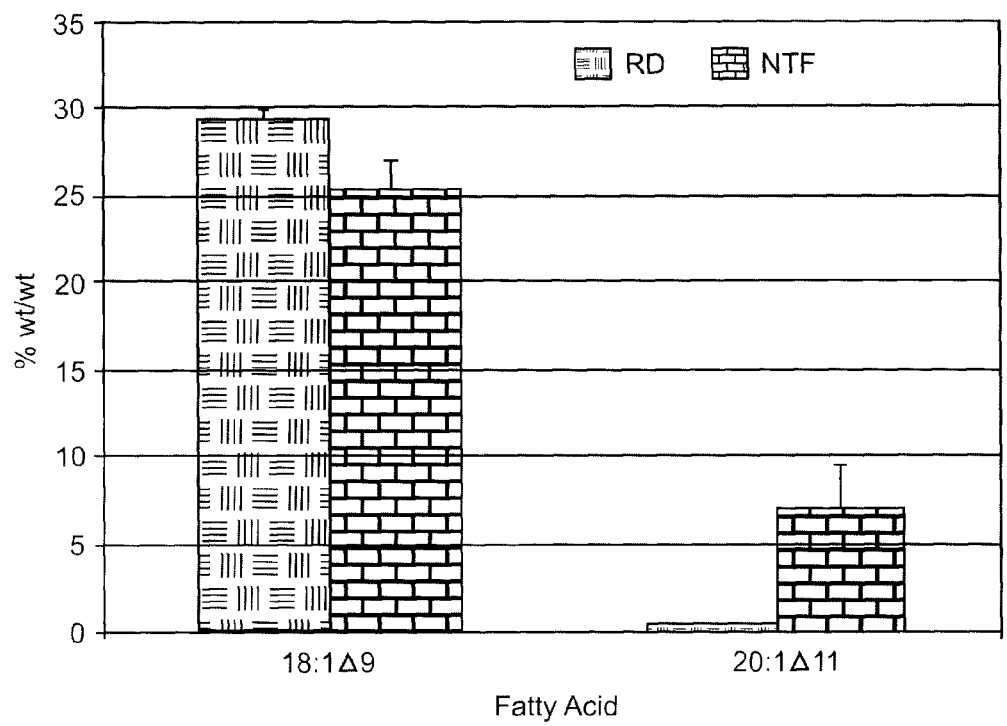
FIG. 13. Fatty acid composition of transgenic *Arabidopsis* (fae1 mutant line) $T_2$ seed oils. Results represent the average from 36 independent lines. Construct: RD-control (plasmid only), NTF-Napin: *Teesdalia* FAE.
Figure 14:
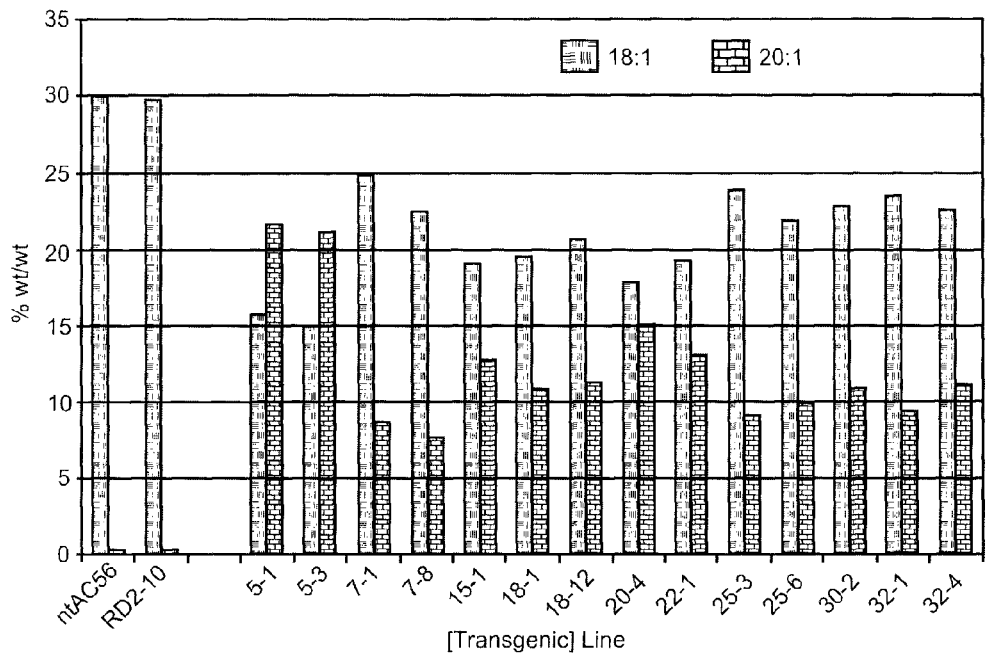
FIG. 14. Fatty acid composition of transgenic *Arabidopsis* $T_3$ seed oils. Proportion of 18:1 Δ9 and 20:1 Δ11 in seed oils from nontransformed *Arabidopsis* fae1 mutant line (ntAC56), plasmid only transgenic control line (RD2-10) and the 14 best *Arabidopsis* transgenic lines expressing *T. nudicaulis* FAE gene under control of napin promoter. The values are the average±SD of three determinations.

From vacuum-infiltration experiments, 36 kanamycin resistant T$_1$ plants were selected. The T$_2$ progeny were collected individually from each plant and the fatty acid composition determined. Significant changes in fatty acid composition in comparison to the wild type (empty vector) were found. On average the proportion of eicosenoic acid (20:1 Δ11) increased from 0.4% in the wild type mutant line up to 6.93% in T$_2$ transgenic seeds at the expense of 18:1 (FIG. 13). Homozygous T$_3$ lines were analyzed to examine the range of fatty acid proportional redistribution induced by expression of T. nudicaulis FAE. The 14 best T$_3$ lines are shown in FIG. 14. The eicosenoic acid content was increased by up to 70-fold in lines 5-1 and 5-3. The very high level of 20:1 was generally correlated with the concomitant reduction in the proportion of its corresponding elongase primer: 18:1 Δ9. The level of VLCFA increased from 1.6% in the mutant AC56 line to as high as 29.26% in best transgenic line.

EXAMPLE 10

Heterologous Expression of the T. nudicaulis FAE HEAR Brassicaceae

Figure 15:
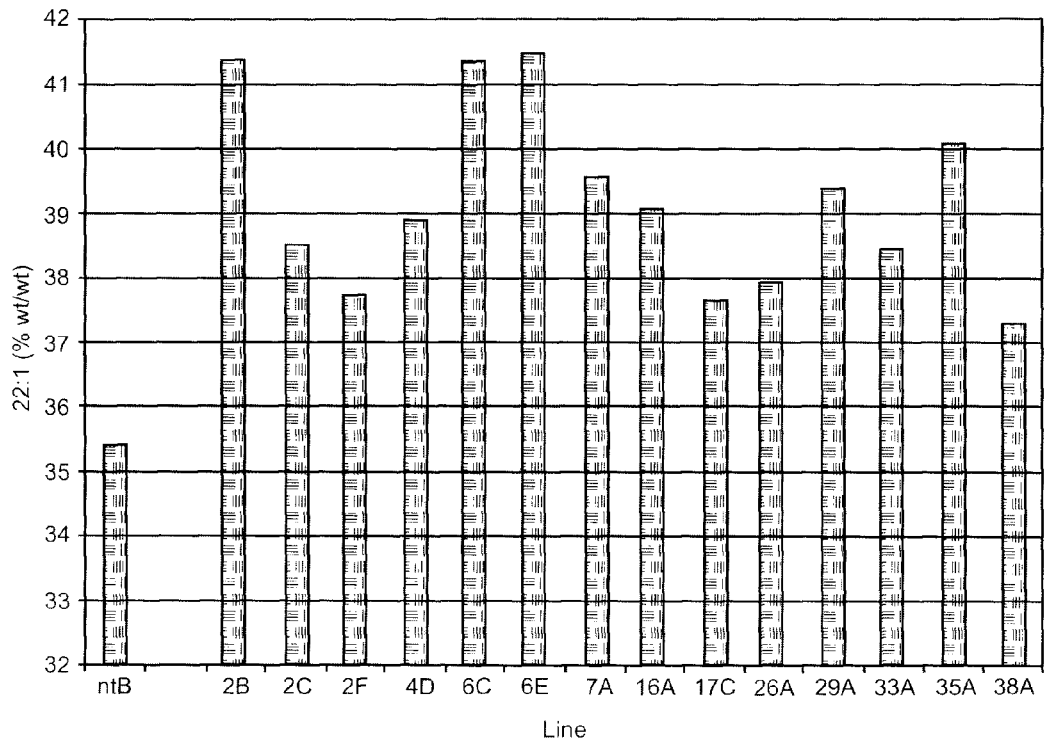
FIG. 15. The accumulation of erucic acid (22:1) in $T_1$ mature seeds of non-transformed *Brassica carinata* wild-type control (ntB) and *B. carinata* transformed with the *Teesdalia nudicaulis* FAE (Lines 2B through 38A).

Seed specific expression of T. nudicaulis FAE in HEAR Brassicaceae (e.g. B. carinata) resulted in increased proportion of erucic acid. The level of erucic acid (22:1 Δ13) was increased from 35.9% in the wild type background to as high as 41.47% in the best T$_1$ transgenic line (FIG. 15).

Conclusion

The fatty acid elongase (FAE), 3-ketoacyl-CoA synthase (KCS) is the first component of the elongation complex involved in synthesis of eicosenoic (20:1) and nervonic acid (24:1) in the seeds of Teesdalia nudicaulis, Lunaria annua and Cardamine graeca. Using a PCR approach, a genomic DNA of an embryo FAE was obtained and heterologously expressed in yeast and in plants. Our results indicate that the L. annua and C. graeca FAE genes encode a condensing enzyme involved in the biosynthesis of very long chain monounsaturated fatty acid, nervonic acid (24:1) utilizing monounsaturated acyl substrates as 20:1 and 22:1. Results from heterologous expression *T. nudicaulis* FAE in yeast as well as in plant system showed that isolated FAE homolog is involved in the biosynthesis of eicosenoic acid (20:1). Thus, the *L. annua* and *C. graeca* FAE homologs in combination with *T. nudicaulis* FAE have a strong engineering impact when expressed in a seed-specific manner in High-erucic acid (H.E.A.) Brassicaceae (e.g. *B. napus* or *B. carinata*) wherein 18:1 Δ9, and 20:1 Δ11 and 22:1 Δ13 represent a rich acyl-CoA elongation substrate pool for biosynthesis of nervonic acid, 24:1 Δ15. The result is the production of seed oils highly enriched in nervonic acid, which are highly values as a pharmaceutical and/or neutraceutical or a nutritional feedstock. In addition, heterologous expression of these FAE genes in HEAR Brassicaceae can be combined with other genetic modifications we have made to enhance the VLCFMA content of HEAR germplasm (15), to provide new industrial feedstock oils of high value and applicability.

References

1. Coupland K. 1996. Nervonic acid composition. PCT PUB. NO.: WO96/05740.
2. Coupland K. and Yann R. (2001) Nervonic acid derivatives, their preparation and use. Canadian Patent Application No.: CA2391953.
3. Coupland K. and Langley N. (1991) Use of Nervonic Acid and long chain fatty acids for the treatment of demyelinating disorders. International Publication No.: WO 91/07955.
4. Sargent J. R., Coupland K. and Wilson R. (1994) Nervonic Acid and Demyelinating Disease. *Medical Hypotheses* 42: 237-242.
5. Nicholls F. H. (1996) New crops in the UK: from concept to bottom line profits. In: *Progress in New Crops*, Janick, J. (Ed.), ASHS Press, Alexandria, Va.
6. Appelqvist L. A. (1976) Lipids in Cruciferae. In: *The Biology and the Chemistry of the CRUCIFERAE*, Vaughan, J. G. and Macleod, A. J. (Eds.), Academic Press, London, UK, pp. 221-277.
7. Meier zu Beerentrup H. and Röbbelen G. (1987) Screening for European production of oilseeds with unusual fatty acids. *Angew. Botanik* 61: 287-303.
8. Van Soest L. J. M. (1994) Alternative crop developments in the Netherlands. Alternative Oilseed and Fibre Crops for Cool and Wet Regions of Europe. Proceedings of a Workshop, 7-8 Apr. 1994 at Wageningen, the Netherlands, pp. 14-20.
9. Mastebroek H. D. and Marvin H. J. P. (2000) Breeding prospects of *Lunaria annua* L. Industrial Crops and Products 11: 139-143.
10. Lange W. and Marvin H. J. P. (2000) Vegetable Oils with Specific Fatty Acids (VOSFA) Agricultural and Industrial Development of Novel Oilseed crops—Final Summary Report, Contract No AIR-CT93-1817.
11. Jart A. (1978) The fatty Acid Composition of various Cruciferous Seeds. *J. Amer. Oil. Chem. Soc.* 55: 873-875.
12. Bettger W. (2000) Apparent Transfer Efficiency of Nervonic Acid from Diet to Milk in dairy Cows and the Subsequent Enrichment of Nervonic Acid in Skim Milk-Based Dairy Products. Special research Funds 2000, University of Guelf, ONT, Canada.
13. Lassner M. V. (1997) Transgenic oilseed crops: a transition from basic research to product development. *Lipid Technology*, 9(1), 5-9.
14. Katavic V., Friesen W., Barton D. L., Gossen K. K., Giblin E. M., Luciw T., An J., Zou J-T., MacKenzie S. L., Keller W. A., Males, D. and Taylor D. C. (2001) Improving erucic acid content in rapeseed through biotechnology: what can the *Arabidopsis* FAE1 and the yeast SLC1-1 genes contribute? *Crop Science* 41, 739-747.
15. Taylor D. C., Katavic V., Zou J-T., MacKenzie S L., Keller W A., An J., Friesen W., Barton D L., Gossen K K., Giblin EM., Ge Y., Dauk M., Luciw T. and Males D. (2001) Field-testing of transgenic rapeseed cv. Hero transformed with a yeast sn-2 acyltransferase results in increased oil content, erucic acid content and seed yield. *Mol Breeding* 8: 317-322.
16. Ghanevati M. and Jaworski J. G. (2001) Active-site residues of a plant membrane-bound fatty acid elongase β-ketoacyl-CoA synthase, FAE1 KCS. *Bioch. et Bioph. Acta* 1530, 77-85.
17. Bradford M. M. (1976) A rapid and sensitive method for the quantitation of microgram quantities of protein utilizing the principle of protein-dye binding. *Anal. Biochem.* 72, 248-254.
18. Katavic V., Barton D. L., Giblin, E. M, Reed D. W., Kumar A. and Taylor D. C. (2004) Gaining insight into the role of serine 282 in *B. napus* FAE1 condensing enzyme. *FEBS Letters* 562: 118-124.
19. Katavic V., Reed D. W., Taylor D. C., Giblin E. M., Barton D. L., Zou J-T., MacKenzie S. L., Covello P. S, and Kunst L. (1995) Alteration of seed fatty acid composition by an ethyl methanesulfonate-induced mutation in *Arabidopsis thaliana* affecting diacylglycerol acyltransferase activity. *Plant Physiol.* 108, 399-409.
20. Altschul S. F., Gish W., Miller W., Myers E. W. and Lipman D. J. (1990) Basic local alignment search tool. *J Mol Biol* 215: 403-410.
21. Persson B. and Argos P. (1994) Prediction of transmembrane segments in proteins utilizing multiple sequence alignments. *J Mol Biol* 237: 182-192.
22. Clough S. J. and Bent A. F. (1998) Floral dip: a simplified method for *Agrobacterium*-mediated transformation of *Arabidopsis thaliana*. *Plant J* 16: 735-743.
23. Mietkiewska E., Giblin E. M., Wang S., Barton D. L., Dirpaul J., Brost J. M., Katavic V. and Taylor D. C. (2004) Seed-specific heterologous expression of a nasturtium FAE gene in *Arabidopsis* results in a dramatic increase in the proportion of erucic acid. *Plant Physiol* 136: 2665-2675.
24. Babic V., Datla R. S., Scoles G. J. and Keller W. A (1998) Development of an efficient *Agrobacterium*-mediated transformation system for *Brassica carinata*. *Plant Cell Reports* 17: 183-188.
25. Jako C., Kumar A., Wei Y., Zou J-T., Barton D. L., Giblin E. M., Covello P. S. and Taylor D. C. (2001) Seed-specific over-expression of an *Arabidopsis thaliana* cDNA encoding a diacylglycerol acyltransferase enhances seed oil content and seed weight. *Plant Physiol* 126: 861-874.
26. Koncz C. and Schell J. (1986) The promoter of $T_L$-DNA gene 5 controls the tissue-specific expression of chimaeric genes by a novel type of *Agrobacterium* binary vector. *Mol Gen Genet* 204: 383-396.
27. Chen J., Greenblatt I. M. and Dellaporta S. L. (1992) Molecular analysis of Ac transposition and DNA replication. *Genetics* 130: 665-676.

The invention claimed is:

1. An isolated nucleic acid molecule comprising the nucleotide sequence of SEQ ID NO: 5, SEQ ID NO: 6 or SEQ ID NO: 13 that encodes a fatty acid elongase (FAE) protein.

2. A cell containing one or more heterologous nucleic acid molecules comprising the nucleotide sequence of SEQ ID NO: 5, SEQ ID NO: 6, SEQ ID NO: 13 or a combination thereof that encode a fatty acid elongase protein.

3. The cell of claim 2 which is a plant cell.

4. The cell of claim 3, wherein the plant cell is a cell of *Arabidopsis, Brassica carinata, Brassica juncea, Brassica napus* or *Camelina sativa*.

5. The cell of claim 3, wherein the plant cell is a cell of borage, Canola, castor, cocoa bean, corn, cotton, *Crambe* spp., *Cuphea* spp., flax, *Lesquerella* spp., *Limnanthes* spp., Linola, nasturtium, *Oenothera* spp., olive, palm, peanut, rapeseed, safflower, soybean, sunflower, tobacco, *Vernonia* spp., wheat, barley, rice, oat, sorghum or rye.

6. The cell of claim 2 having 1.5× or more nervonic acid (24:1 Δ15) and/or eicosenoic acid (20:1 Δ11) than a control cell lacking the one or more heterologous nucleic acid molecules.

7. A plant seed containing one or more heterologous nucleic acid molecules comprising the nucleotide sequence of SEQ ID NO: 5, SEQ ID NO: 6, SEQ ID NO: 13 or a combination thereof that encode a fatty acid elongase protein.

8. The seed of claim 7, which is a seed from *Arabidopsis, Brassica carinata, Brassica juncea, Brassica napus* or *Camelina sativa*.

9. The seed of claim 7, which is a seed from borage, Canola, castor, cocoa bean, corn, cotton, *Crambe* spp., *Cuphea* spp., flax, *Lesquerella* spp., *Limnanthes* spp., Linola, nasturtium, *Oenothera* spp., olive, palm, peanut, rapeseed, safflower, soybean, tobacco, *Vernonia* spp., wheat, barley, rice, oat, sorghum or rye.

10. The seed of claim 7 having 1.5× or more nervonic acid (24:1 Δ15) and/or eicosenoic acid (20:1 Δ11) than a control cell lacking the one or more heterologous nucleic acid molecules.

11. A plant comprising one or more heterologous nucleic acid molecules comprising the nucleotide sequence of SEQ ID NO: 5, SEQ ID NO: 6, SEQ ID NO: 13 or a combination thereof that encode a fatty acid elongase protein.

12. The plant of claim 11, which is *Arabidopsis, Brassica carinata, Brassica juncea, Brassica napus* or *Camelina sativa*.

13. The plant of claim 11, which is borage, Canola, castor, cocoa bean, corn, cotton, *Crambe* spp., *Cuphea* spp., flax, *Lesquerella* spp., *Limnanthes* spp., Linola, nasturtium, *Oenothera* spp., olive, palm, peanut, rapeseed, safflower, soybean, sunflower, tobacco, *Vernonia* spp., wheat, barley, rice, oat, sorghum or rye.

14. The plant of claim 11 having 1.5× or more nervonic acid (24:1 Δ15) and/or eicosenoic acid (20:1 Δ11) than a control cell lacking the one or more heterologous nucleic acid molecules.

15. A process for increasing levels of very long chain monounsaturated fatty acids in a seed oil of a plant seed beyond that of a control seed, the process comprising: transgenically expressing one or more fatty acid elonqase polypeptides selected from the group consisting of SEQ ID NO: 7, SEQ ID NO: 8 and SEQ ID NO: 14 in a plant producing the seed, the control seed lacking expression of the fatty acid elonqase polypeptides.

16. The process of claim 15, wherein the very long chain monounsaturated fatty acids whose levels are increased are nervonic acid (24:1 Δ15) and/or eicosenoic acid (20:1 Δ11).

17. The process of claim 15, wherein the very long chain monounsaturated fatty acid whose level is increased is nervonic acid (24:1 Δ15).

18. The process of claim 15, wherein the plant seed is a seed from *Arabidopsis, Brassica carinata, Brassica juncea, Brassica napus* or *Camelina sativa*.

19. The process of claim 15, wherein the plant seed is a seed from borage, Canola, castor, cocoa bean, corn, cotton, *Crambe* spp., *Cuphea* spp., flax, *Lesquerella* spp., *Limnanthes* spp., Linola, nasturtium, *Oenothera* spp., olive, palm, peanut, rapeseed, safflower, soybean, sunflower, tobacco, *Vernonia* spp., wheat, barley, rice, oat, sorghum or rye.

20. The process of claim 15, wherein the level is increased 1.5× or more beyond that of the control seed.

21. The process of claim 15, wherein the level is increased 2× or more beyond that of the control seed.

22. The process of claim 15, wherein the level is increased 5× or more beyond that of the control seed.

23. A process of obtaining seeds comprising: a) transforming a plant cell with a recombinant nucleic acid construct comprising a nucleic acid molecule comprising the nucleotide sequence of SEQ ID NO: 5, SEQ ID NO: 6 or SEQ ID NO: 13 that encodes a fatty acid elongase protein and a promoter for driving expression of the nucleic acid molecule in the plant cell to form a transformed plant; b) regenerating the transformed plant for one or more generations; and, c) harvesting seeds from cultivated plants produced in part b).

* * * * *

SEQUENCE LISTING

<160> NUMBER OF SEQ ID NOS: 16

<210> SEQ ID NO 1
<211> LENGTH: 39
<212> TYPE: DNA
<213> ORGANISM: Artificial Sequence
<220> FEATURE:
<223> OTHER INFORMATION: Primer

<400> SEQUENCE: 1
atgacgtcca ttaacgtaaa gctcctttac cattacgtc                           39

<210> SEQ ID NO 2
<211> LENGTH: 32
<212> TYPE: DNA
<213> ORGANISM: Artificial Sequence
<220> FEATURE:
<223> OTHER INFORMATION: Primer

<400> SEQUENCE: 2
ttaggaccga ccgttttggg cacgagtctc tg                                  32

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
atgacgtcca ttaacgtaaa gctcc                                          25

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
ttaggaccga ccgttttggg c                                              21

<210> SEQ ID NO 5
<211> LENGTH: 1518
<212> TYPE: DNA
<213> ORGANISM: Lunaria annua

<400> SEQUENCE: 5
atgacgtcca ttaacgtaaa gctcctttac cattacgtca taaccaactt tttcaacctc    60
tgtttcttcc cactgacggc gatcctcgcc ggaaaagcct ctcgtcttac cacaaacgat   120
ctccaccact tctattcata tctccaacac aaccttataa ccttaaccct actctttgcc   180
ttcaccgttt ttggttcggt tctctacttc gtaacccgac ccaaaccggt ttacctcgtt   240
gactactcct gctaccttcc accacaacat cttagcgctg gtatctctaa gaccatggaa   300
atcttttatc aaataagaaa atctgatcct ttacgaaacg tggcattaga tgattcgtct   360
tctcttgatt tcttgagaaa gattcaagag cgttcaggtc taggcgatga aacctacggc   420
cccgagggac tgtttgagat tcctccgagg aagaatttag cgtcggcgcg tgaagagacg   480
gagcaagtaa tcaacggtgc gctaaaaaat ctattcgaga acaccaaagt taaccctaaa   540
gagattggta tacttgtggt gaactcaagc atgtttaatc cgactccttc gttatccgcg   600

-continued

| | |
|---|---|
| atggtagtta atactttcaa gctccgaagc aacatcaaaa gctttaatct tggaggaatg | 660 |
| ggttgcagtg ctggtgttat cgccattgat ctagctaaag acttgttgca tgttcataaa | 720 |
| aacacatatg ctcttgtggt gagcacagag aacatcactc aaaacattta taccggtgat | 780 |
| aacagatcca tgatggtttc gaattgcttg ttccgtgtcg gtggggcagc gattctgctc | 840 |
| tccaacaagc cggggatcg aagacggtcc aagtacaggc tagctcacac ggttcgaacg | 900 |
| cataccggag ctgacgacaa gtcttttgga tgtgtgcggc aagaagaaga tgatagcggt | 960 |
| aaaaccggag ttagtttgtc aaaagacata accggtgttg ccgggataac ggttcagaaa | 1020 |
| aacataacaa cattgggtcc gttggttctt cctctgagcg aaaaaatcct tttgtcgtt | 1080 |
| acattcgtag ccaagaaact attaaaagat aagatcaaac actattacgt gccggatttc | 1140 |
| aaacttgcag tagatcattt ctgtattcat gcgggaggta gagccgtgat agatgtgtta | 1200 |
| gagaagaact tagggctatc gccgatagat gtggaggcat caagatcaac attacataga | 1260 |
| tttgggaata catcgtctag ttcaatttgg tatgaattag catacataga ggcaaaagga | 1320 |
| aggatgaaga aaggtaataa agcttggcaa atagctgttg ggtcaggttt taagtgtaat | 1380 |
| agtgcggttt gggtcgcttt acgcaatgtc aaggcttcag ctaatagtcc ttgggaacat | 1440 |
| tgcattcaca aatatccggt tcagatgtat tctggttcat caaagtcaga gactcgtgcc | 1500 |
| caaaacggtc ggtcctaa | 1518 |

<210> SEQ ID NO 6
<211> LENGTH: 1521
<212> TYPE: DNA
<213> ORGANISM: Cardamine graeca

<400> SEQUENCE: 6

| | |
|---|---|
| atgacgtcca ttaacgtaaa gctccttac cattacgtcc ttaccaactt tttcaacctc | 60 |
| tgtttgttcc cgttaacggc gttccctgcc ggaaaagcct ctcagcttac tacaaacgat | 120 |
| ctccaccact tatattccta tctccaccac aaccttataa ccgttactct actctttgct | 180 |
| ttcaccgttt tcggttcgat tctctacatc gtaacccgac ccaaaccggt ttacctcgtt | 240 |
| gactattcct gctaccttcc tccacgtcat ctcagttgtg gtatctctag ggtaatggaa | 300 |
| attttctatg aaataaggaa atctgatcct tctcgcgagg tgccatttga tgatccgtct | 360 |
| tcgcttgaat tctgaggaa gattcaagaa cgttcaggtc taggtgatga aacctacggt | 420 |
| cctcaaggac tcgttcatga tatgccacta cggatgaatt ttgcggcggc acgtgaagag | 480 |
| acagagcaag taatcaacgg tgcgctcgaa aaactattcg agaacaccaa agttaaccct | 540 |
| agagagattg gtatacttgt ggtgaattca agcatgttta atccaactcc ttcgctgtcg | 600 |
| gcgatggtcg ttaatacatt caagctccga agcaacatca agagctttag tcttgggggc | 660 |
| atgggttgta gtgctggtat tatcgccatt gatcttgcta aagacttgtt gcatgttcac | 720 |
| aaaaacactt atgctcttgt ggttagcaca gagaacatca ctcacagcac ttatactggt | 780 |
| gataatagat ccatgatggt ttcaaattgc ttgttccgta tgggtggggc cgcgattttg | 840 |
| ctctctaaca aggcgggaga tcgaagacgg tccaagtaca agctagctca cacggttcga | 900 |
| acgcataccg gagccgacga tcagtctttt cgatgtgttc gtcaagaaga cgatgataga | 960 |
| ggaaaaatcg gagtttgttt gtccaaggac ataacagctg ttgcagggaa aacggttacg | 1020 |
| aaaaacatag caacattggg tccgttggtt cttcctttga gcgaaaagtt tctttatgtc | 1080 |
| gtttccttga tggccaagaa acttttcaag aacaagatca agcacactta cgtcccggat | 1140 |
| ttcaaacttg ctattgacca ttttttgtatc catgctggag gcagagccgt gatcgacgtg | 1200 |

-continued

```
cttgagaaga acttagcgct atcaccggtt gacgtggagg catcaagatc aacgttacat    1260
agatttggga atacttcgtc tagctcaatt tggtatgaat tggcatacat agaggcaaaa    1320
ggaaggatga agaaagggaa taaagtttgg cagatagcta tagggtcagg gtttaagtgt    1380
aatagtgcgg tttgggtggc tctatgcaat gtcaagcctt cggtaaacag tccatgggaa    1440
cattgcatcg atagatatcc tgttgagatt aactatggtt cgtcaaagtc agagactcgt    1500
gcccaaaacg gtcggtccta a                                              1521
```

<210> SEQ ID NO 7
<211> LENGTH: 505
<212> TYPE: PRT
<213> ORGANISM: Lunaria annua

<400> SEQUENCE: 7

```
Met Thr Ser Ile Asn Val Lys Leu Leu Tyr His Tyr Val Ile Thr Asn
  1               5                  10                  15

Phe Phe Asn Leu Cys Phe Phe Pro Leu Thr Ala Ile Leu Ala Gly Lys
                 20                  25                  30

Ala Ser Arg Leu Thr Thr Asn Asp Leu His His Phe Tyr Ser Tyr Leu
             35                  40                  45

Gln His Asn Leu Ile Thr Leu Thr Leu Leu Phe Ala Phe Thr Val Phe
         50                  55                  60

Gly Ser Val Leu Tyr Phe Val Thr Arg Pro Lys Pro Val Tyr Leu Val
 65                  70                  75                  80

Asp Tyr Ser Cys Tyr Leu Pro Pro Gln His Leu Ser Ala Gly Ile Ser
                 85                  90                  95

Lys Thr Met Glu Ile Phe Tyr Gln Ile Arg Lys Ser Asp Pro Leu Arg
            100                 105                 110

Asn Val Ala Leu Asp Asp Ser Ser Leu Asp Phe Leu Arg Lys Ile
        115                 120                 125

Gln Glu Arg Ser Gly Leu Gly Asp Glu Thr Tyr Gly Pro Glu Gly Leu
    130                 135                 140

Phe Glu Ile Pro Pro Arg Lys Asn Leu Ala Ser Ala Arg Glu Glu Thr
145                 150                 155                 160

Glu Gln Val Ile Asn Gly Ala Leu Lys Asn Leu Phe Glu Asn Thr Lys
                165                 170                 175

Val Asn Pro Lys Glu Ile Gly Ile Leu Val Val Asn Ser Ser Met Phe
            180                 185                 190

Asn Pro Thr Pro Ser Leu Ser Ala Met Val Val Asn Thr Phe Lys Leu
        195                 200                 205

Arg Ser Asn Ile Lys Ser Phe Asn Leu Gly Gly Met Gly Cys Ser Ala
    210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr Gln Asn Ile
                245                 250                 255

Tyr Thr Gly Asp Asn Arg Ser Met Met Val Ser Asn Cys Leu Phe Arg
            260                 265                 270

Val Gly Gly Ala Ala Ile Leu Leu Ser Asn Lys Pro Gly Asp Arg Arg
        275                 280                 285

Arg Ser Lys Tyr Arg Leu Ala His Thr Val Arg Thr His Thr Gly Ala
    290                 295                 300

Asp Asp Lys Ser Phe Gly Cys Val Arg Gln Glu Glu Asp Asp Ser Gly
305                 310                 315                 320
```

```
Lys Thr Gly Val Ser Leu Ser Lys Asp Ile Thr Gly Val Ala Gly Ile
                325                 330                 335

Thr Val Gln Lys Asn Ile Thr Leu Gly Pro Leu Val Leu Pro Leu
            340                 345                 350

Ser Glu Lys Ile Leu Phe Val Val Thr Phe Val Ala Lys Lys Leu Leu
        355                 360                 365

Lys Asp Lys Ile Lys His Tyr Tyr Val Pro Asp Phe Lys Leu Ala Val
    370                 375                 380

Asp His Phe Cys Ile His Ala Gly Gly Arg Ala Val Ile Asp Val Leu
385                 390                 395                 400

Glu Lys Asn Leu Gly Leu Ser Pro Ile Asp Val Glu Ala Ser Arg Ser
                405                 410                 415

Thr Leu His Arg Phe Gly Asn Thr Ser Ser Ser Ile Trp Tyr Glu
            420                 425                 430

Leu Ala Tyr Ile Glu Ala Lys Gly Arg Met Lys Lys Gly Asn Lys Ala
        435                 440                 445

Trp Gln Ile Ala Val Gly Ser Gly Phe Lys Cys Asn Ser Ala Val Trp
    450                 455                 460

Val Ala Leu Arg Asn Val Lys Ala Ser Ala Asn Ser Pro Trp Glu His
465                 470                 475                 480

Cys Ile His Lys Tyr Pro Val Gln Met Tyr Ser Gly Ser Ser Lys Ser
                485                 490                 495

Glu Thr Arg Ala Gln Asn Gly Arg Ser
                500                 505

<210> SEQ ID NO 8
<211> LENGTH: 506
<212> TYPE: PRT
<213> ORGANISM: Cardamine graeca

<400> SEQUENCE: 8

Met Thr Ser Ile Asn Val Lys Leu Leu Tyr His Tyr Val Leu Thr Asn
1               5                   10                  15

Phe Phe Asn Leu Cys Leu Phe Pro Leu Thr Ala Phe Pro Ala Gly Lys
            20                  25                  30

Ala Ser Gln Leu Thr Thr Asn Asp Leu His His Leu Tyr Ser Tyr Leu
        35                  40                  45

His His Asn Leu Ile Thr Val Thr Leu Leu Phe Ala Phe Thr Val Phe
    50                  55                  60

Gly Ser Ile Leu Tyr Ile Val Thr Arg Pro Lys Pro Val Tyr Leu Val
65                  70                  75                  80

Asp Tyr Ser Cys Tyr Leu Pro Pro Arg His Leu Ser Cys Gly Ile Ser
                85                  90                  95

Arg Val Met Glu Ile Phe Tyr Glu Ile Arg Lys Ser Asp Pro Ser Arg
            100                 105                 110

Glu Val Pro Phe Asp Asp Pro Ser Ser Leu Glu Phe Leu Arg Lys Ile
        115                 120                 125

Gln Glu Arg Ser Gly Leu Gly Asp Glu Thr Tyr Gly Pro Gln Gly Leu
    130                 135                 140

Val His Asp Met Pro Leu Arg Met Asn Phe Ala Ala Ala Arg Glu Glu
145                 150                 155                 160

Thr Glu Gln Val Ile Asn Gly Ala Leu Glu Lys Leu Phe Glu Asn Thr
                165                 170                 175

Lys Val Asn Pro Arg Glu Ile Gly Ile Leu Val Val Asn Ser Ser Met
            180                 185                 190
```

```
Phe Asn Pro Thr Pro Ser Leu Ser Ala Met Val Val Asn Thr Phe Lys
        195                 200                 205
Leu Arg Ser Asn Ile Lys Ser Phe Ser Leu Gly Gly Met Gly Cys Ser
    210                 215                 220
Ala Gly Ile Ile Ala Ile Asp Leu Ala Lys Asp Leu Leu His Val His
225                 230                 235                 240
Lys Asn Thr Tyr Ala Leu Val Val Ser Thr Glu Asn Ile Thr His Ser
                245                 250                 255
Thr Tyr Thr Gly Asp Asn Arg Ser Met Met Val Ser Asn Cys Leu Phe
            260                 265                 270
Arg Met Gly Gly Ala Ala Ile Leu Leu Ser Asn Lys Ala Gly Asp Arg
        275                 280                 285
Arg Arg Ser Lys Tyr Lys Leu Ala His Thr Val Arg Thr His Thr Gly
        290                 295                 300
Ala Asp Asp Gln Ser Phe Arg Cys Val Arg Gln Glu Asp Asp Arg
305                 310                 315                 320
Gly Lys Ile Gly Val Cys Leu Ser Lys Asp Ile Thr Ala Val Ala Gly
                325                 330                 335
Lys Thr Val Thr Lys Asn Ile Ala Thr Leu Gly Pro Leu Val Leu Pro
            340                 345                 350
Leu Ser Glu Lys Phe Leu Tyr Val Val Ser Leu Met Ala Lys Lys Leu
        355                 360                 365
Phe Lys Asn Lys Ile Lys His Thr Tyr Val Pro Asp Phe Lys Leu Ala
        370                 375                 380
Ile Asp His Phe Cys Ile His Ala Gly Gly Arg Ala Val Ile Asp Val
385                 390                 395                 400
Leu Glu Lys Asn Leu Ala Leu Ser Pro Val Asp Val Glu Ala Ser Arg
                405                 410                 415
Ser Thr Leu His Arg Phe Gly Asn Thr Ser Ser Ser Ile Trp Tyr
            420                 425                 430
Glu Leu Ala Tyr Ile Glu Ala Lys Gly Arg Met Lys Lys Gly Asn Lys
        435                 440                 445
Val Trp Gln Ile Ala Ile Gly Ser Gly Phe Lys Cys Asn Ser Ala Val
        450                 455                 460
Trp Val Ala Leu Cys Asn Val Lys Pro Ser Val Asn Ser Pro Trp Glu
465                 470                 475                 480
His Cys Ile Asp Arg Tyr Pro Val Glu Ile Asn Tyr Gly Ser Ser Lys
                485                 490                 495
Ser Glu Thr Arg Ala Gln Asn Gly Arg Ser
            500                 505

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
gctctagaat gacgtccatt aacgtaa                                            27

<210> SEQ ID NO 10
<211> LENGTH: 24
<212> TYPE: DNA
<213> ORGANISM: Artificial Sequence
<220> FEATURE:
<223> OTHER INFORMATION: Primer
```

-continued

```
<400> SEQUENCE: 10
ggggtacctt aggaccgacc gttt                                          24

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
gcaatgacgt ccgttaacgt taag                                          24

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
ggaccgaccg ttttggac                                                 18

<210> SEQ ID NO 13
<211> LENGTH: 1521
<212> TYPE: DNA
<213> ORGANISM: Teesdalia nudicaulis

<400> SEQUENCE: 13
atgacgtccg ttaacgttaa gtttatttac cattacgtca tcaccaactt tttcaacctt     60
tgcttcttcc ctttatcggc aatcctcgcc gggaaagcct cccgtttcac cacgaacgac    120
ctccacatct tttattactc atatctccta caaaacatta taacccttac tatactattt    180
tcattaaccg ctttcggttt ggttctctac attgtaacca aaccaaaacc ggtttacctc    240
gttgactact cttgctacct tccaccacct catcatagag taagtgtctc caaggtattg    300
gatatcttct accaagtaaa aaaagctgac cctttaagga acggttcaag cgatgactct    360
tcatggttag acttcttgag gaaaattcaa gaacgttcgg gtctcgggga cgaaactcac    420
gccccagagg gatttcttca ggttccacca cgaacatctt tcgggcggc acgtgaagaa     480 accgagcatg ttatcatcgg agcggtcaaa accttgtttg aaaacacaaa agtgaaccct    540
aaagatattg gtatacttgt ggtgaattca agcttgttta atccaactcc ttcgttatca    600
gcaatggttg ttaatacttt taagcttcga agcaacataa gaagctttag tcttggtgga    660
atgggttgta gtgctggtgt tatagctatt gatctagcta agacttgtt gcatgttcat     720 aaaaacactt atgctctagt ggttagtacg gagaacatca ctcgtagtat ttatgctggt    780
gacaataaat ccatgatggt ttcaaactgt ttgtttcgcg tgggtggggc cgcggttttg    840
ctttctaaca agccgggaga tcagagtagg tctaagtaca agctagctca tacgttaggg   900
acacataccg gagccgatga caaatgtttt caatgtgttc aacaagaaga tgatgagagt   960
ggtaaaaccg gtgtttcttt gtctaaagac ataaccactg tcgctggaag aacagttcaa  1020
aagaacataa caacgttaag tcctttaatt cttccttta gcgaaaaatt tctatttttc   1080
gtaaccttca tcggcaagaa actatttaaa gacaaaatca gagttacta cgttccggat   1140 tttaagctag ctattgatca ttttgtatc catgcgggag ggagagcggt tatcgatgtg    1200
ctagagaaga acttaggact atctcctgtt gatgtcgaag cgtctaggtc aacgttacat   1260
aggtttggta atacttcatc tagctcaata tggtatgaat tggcatatat tgaagctaaa    1320
```

-continued

```
ggaaggatga agaaagggaa taaagcatgg caaattgctt taggttcagg ctttaagtgc    1380
aatagtgcag tttgggtagc tttacgcaat gttaaggctt ccaagagtag tccttgggaa    1440
cattgcattg acaaatatcc ggttaatatt gattctgatt ctgttaagtc agagactcgt    1500
gtccaaaacg gtcggtccta a                                              1521
```

<210> SEQ ID NO 14
<211> LENGTH: 506
<212> TYPE: PRT
<213> ORGANISM: Teesdalia nudicaulis

<400> SEQUENCE: 14

```
Met Thr Ser Val Asn Val Lys Phe Ile Tyr His Tyr Val Ile Thr Asn
1               5                   10                  15

Phe Phe Asn Leu Cys Phe Phe Pro Leu Ser Ala Ile Leu Ala Gly Lys
            20                  25                  30

Ala Ser Arg Phe Thr Thr Asn Asp Leu His Ile Phe Tyr Tyr Ser Tyr
        35                  40                  45

Leu Leu Gln Asn Ile Ile Thr Leu Thr Ile Leu Phe Ser Leu Thr Ala
    50                  55                  60

Phe Gly Leu Val Leu Tyr Ile Val Thr Lys Pro Lys Pro Val Tyr Leu
65                  70                  75                  80

Val Asp Tyr Ser Cys Tyr Leu Pro Pro His His Arg Val Ser Val
                85                  90                  95

Ser Lys Val Leu Asp Ile Phe Tyr Gln Val Lys Lys Ala Asp Pro Leu
            100                 105                 110

Arg Asn Gly Ser Ser Asp Asp Ser Ser Trp Leu Asp Phe Leu Arg Lys
        115                 120                 125

Ile Gln Glu Arg Ser Gly Leu Gly Asp Glu Thr His Ala Pro Glu Gly
    130                 135                 140

Phe Leu Gln Val Pro Pro Arg Thr Ser Phe Gly Ala Ala Arg Glu Glu
145                 150                 155                 160

Thr Glu His Val Ile Ile Gly Ala Val Lys Thr Leu Phe Glu Asn Thr
                165                 170                 175

Lys Val Asn Pro Lys Asp Ile Gly Ile Leu Val Val Asn Ser Ser Leu
            180                 185                 190

Phe Asn Pro Thr Pro Ser Leu Ser Ala Met Val Asn Thr Phe Lys
        195                 200                 205

Leu Arg Ser Asn Ile Arg Ser Phe Ser Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Arg Ser
                245                 250                 255

Ile Tyr Ala Gly Asp Asn Lys Ser Met Met Val Ser Asn Cys Leu Phe
            260                 265                 270

Arg Val Gly Gly Ala Ala Val Leu Leu Ser Asn Lys Pro Gly Asp Gln
        275                 280                 285

Ser Arg Ser Lys Tyr Lys Leu Ala His Thr Val Arg Thr His Thr Gly
    290                 295                 300

Ala Asp Asp Lys Cys Phe Gln Cys Val Gln Gln Glu Asp Asp Glu Ser
305                 310                 315                 320

Gly Lys Thr Gly Val Ser Leu Ser Lys Asp Ile Thr Thr Val Ala Gly
                325                 330                 335

Arg Thr Val Gln Lys Asn Ile Thr Thr Leu Ser Pro Leu Ile Leu Pro
```

```
                    340                 345                 350
Phe Ser Glu Lys Phe Leu Phe Phe Val Thr Phe Ile Gly Lys Lys Leu
        355                 360                 365
Phe Lys Asp Lys Ile Lys Ser Tyr Tyr Val Pro Asp Phe Lys Leu Ala
        370                 375                 380
Ile Asp His Phe Cys Ile His Ala Gly Gly Arg Ala Val Ile Asp Val
385                 390                 395                 400
Leu Glu Lys Asn Leu Gly Leu Ser Pro Val Asp Val Glu Ala Ser Arg
                405                 410                 415
Ser Thr Leu His Arg Phe Gly Asn Thr Ser Ser Ser Ile Trp Tyr
                420                 425                 430
Glu Leu Ala Tyr Ile Glu Ala Lys Gly Arg Met Lys Lys Gly Asn Lys
        435                 440                 445
Ala Trp Gln Ile Ala Leu Gly Ser Gly Phe Lys Cys Asn Ser Ala Val
        450                 455                 460
Trp Val Ala Leu Arg Asn Val Lys Ala Ser Lys Ser Ser Pro Trp Glu
465                 470                 475                 480
His Cys Ile Asp Lys Tyr Pro Val Asn Ile Asp Ser Asp Ser Val Lys
                485                 490                 495
Ser Glu Thr Arg Val Gln Asn Gly Arg Ser
                500                 505

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15
tatctagaat gacgtccgtt aacgttaag                                      29

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
atggtacctt aggaccgacc gttttgg                                        27
```